United States Patent
Harada

(10) Patent No.: US 8,337,443 B2
(45) Date of Patent: Dec. 25, 2012

(54) APPARATUS FOR CORRECTING AN INGROWN NAIL

(76) Inventor: Masanori Harada, Kitakyushu (JP)

( * ) Notice: Subject to any disclaimer, the term of this patent is extended or adjusted under 35 U.S.C. 154(b) by 825 days.

(21) Appl. No.: 12/085,224

(22) PCT Filed: Feb. 8, 2008

(86) PCT No.: PCT/JP2008/052162
§ 371 (c)(1),
(2), (4) Date: May 20, 2008

(87) PCT Pub. No.: WO2008/142880
PCT Pub. Date: Nov. 27, 2008

(65) Prior Publication Data
US 2010/0137771 A1 Jun. 3, 2010

(30) Foreign Application Priority Data
May 11, 2007 (JP) .................. 2007-127243

(51) Int. Cl.
*A61F 5/00* (2006.01)
(52) U.S. Cl. ................ 602/31; 602/30; 602/23
(58) Field of Classification Search .......... 602/31, 602/30, 23
See application file for complete search history.

(56) References Cited

U.S. PATENT DOCUMENTS

| | | | |
|---|---|---|---|
| 1,708,716 A | 4/1929 | Andersen | |
| 1,772,130 A * | 8/1930 | Crenshaw | 602/31 |
| 2,024,412 A | 12/1935 | Wilson | |
| 3,173,416 A | 3/1965 | Rederich | |
| 4,057,055 A | 11/1977 | Clark | |
| 4,068,656 A | 1/1978 | Barmore | |
| 4,111,779 A | 9/1978 | Seko et al. | |
| 4,295,953 A | 10/1981 | Fuseya et al. | |
| 4,602,984 A | 7/1986 | Beaver et al. | |
| 4,734,180 A | 3/1988 | Sato et al. | |
| 5,012,799 A | 5/1991 | Remmen | |
| 5,225,060 A | 7/1993 | Noaki et al. | |
| 5,571,390 A | 11/1996 | Kimura et al. | |
| 6,050,966 A * | 4/2000 | Wilberscheid | 602/31 |

FOREIGN PATENT DOCUMENTS

| | | |
|---|---|---|
| JP | 54-153389 U | 10/1979 |
| JP | 59-153376 A | 9/1984 |
| JP | 61-19789 A | 1/1986 |
| JP | 63-11686 A | 1/1988 |
| JP | 4-289185 A | 10/1992 |

(Continued)

*Primary Examiner* — Patricia Bianco
*Assistant Examiner* — Victoria J Hicks
(74) *Attorney, Agent, or Firm* — Birch, Stewart, Kolasch & Birch, LLP

(57) ABSTRACT

The present invention provides an apparatus for correcting an ingrown nail within a very short time (30 min to 1 hr) with a very simple operation and without pain. The apparatus contains an upstanding push-down member having at its lower end a push-down head; a laterally extending, lifting angle maintenance means secured at its middle portion to the push-down member; and lifting members (having anchors at their lower ends) extending downwardly from portions of the maintenance means which are opposite relative to the middle portion of the maintenance means at which the push-down member is secured. When the lifting members are placed under tension, the anchors secured to side portions of a nail are lifted to exert a lifting force on the side portions while causing the push-down member to push the middle portion of the nail in its thicknesswise direction.

11 Claims, 8 Drawing Sheets

FOREIGN PATENT DOCUMENTS

| | | |
|---|---|---|
| JP | 4-350190 A | 12/1992 |
| JP | 5-320970 A | 12/1993 |
| JP | 8-215227 A | 8/1996 |
| JP | 10-110287 A | 4/1998 |
| JP | 11-71693 A | 3/1999 |
| JP | 2001-276104 A | 10/2001 |
| JP | 2004-238288 A | 8/2004 |
| JP | 2006-314748 A | 11/2006 |

* cited by examiner

APPARATUS FOR CORRECTING AN INGROWN NAIL

This application is a national stage entry of PCT/JP2008/052162 filed Feb. 8, 2008 and claims priority to Japanese patent 2007-127243 filed May 11, 2007.

FIELD OF THE INVENTION

The present invention relates to an apparatus for correcting an ingrown nail. More particularly, the present invention is concerned with an apparatus for correcting an ingrown nail by lifting a nail edge grown into a nail bed, which comprises: an upstanding push-down member having at a lower end thereof a push-down head; a laterally extending, lifting angle maintenance means which is secured, at a middle portion thereof, to the upstanding push-down member; and a pair of lifting members extending downwardly from respective portions of the lifting angle maintenance means, which portions are opposite relative to the middle portion of the lifting angle maintenance means at which the upstanding push-down member is secured, each lifting member having an anchor at a lower end thereof, wherein, in use of the apparatus, when the lifting members are placed under tension, the anchors which are, respectively, secured to side portions of the outer surface of the nail are lifted to thereby exert an ingrown nail-correcting, lifting force on each of the side portions of the outer surface of the nail while causing the upstanding push-down member to push the middle portion of the outer surface of the nail in the thicknesswise direction of the nail. By the use of the apparatus of the present invention, an ingrown nail can be surely corrected within a very short time, e.g., within about 30 minutes to about 1 hour, with a very simple operation and without causing pain to a patient. Therefore, the apparatus of the present invention is very effective and, hence, has a very high practicality.

BACKGROUND OF THE INVENTION

An ingrown nail (onychocryptosis) is also referred to as a "pincer nail", and is a nail disease where a nail grows or cuts into one or both sides of the nail bed, thus causing a pain which may sometimes be very acute. As examples of causatives of the ingrown nail, there can be mentioned a pressure, an injury, a nail cut to the quick, and a congenital malformation. An ingrown nail is especially likely to occur at a first toenail. As conventional methods for curing the ingrown nail, there are known a method in which the ingrown portion of a nail is surgically removed (hereinafter, frequently referred to as a "surgical removal method"), a method in which a correcting device or a correcting apparatus is used, and a method in which a correction reagent is used. With respect to the methods using a correcting device or apparatus, reference can be made, for example, to U.S. Pat. No. 4,057,055 (Patent Document 1), and Unexamined Japanese Patent Application Laid-Open Specification Nos. Hei 8-215227 (Patent Document 2) and 2001-276104 (Patent Document 3). Further, with respect to the method using a correction reagent, reference can be made to Unexamined Japanese Patent Application Laid-Open Specification No. 2004-238288 (Patent Document 4).

However, the surgical removal method is disadvantageous in that this method is complicated and cumbersome, and the nail plate is permanently narrowed. Further, the surgical removal method has a problem in that, since a part of a nail which has grown or cut into the nail bed is cut away, the operation is difficult in the case where there is a danger of microbial infection. Furthermore, even in the case of the surgical removal method in which a part of the nail is removed to cure the ingrown nail temporarily, a relapse of the ingrown nail often occurs because the nail after the surgery still has an anomalous curvature such that the nail grows again into the nail bed. Therefore, it has been desired to develop a method for correcting an ingrown nail without surgery, i.e., without surgically removing the ingrown portion of the nail.

With respect to the method using a correcting device or apparatus, explanations are made below. For example, Patent Document 1 proposes an apparatus comprising: post members to be secured to lateral side portions of the external surface of a toenail; and a tension member, such as a rubber band, wherein each of the post members has an upstanding portion used for holding the tension member, and wherein the apparatus is so designed that the post members secured to the lateral side portions of the external surface of the toenail are drawn to each other by the tension member to thereby lift the lateral side portions of the nail. Patent Document 2 proposes a method in which a plate made of a shape memory metal or a resin is bent into a curvature and fittedly adhered to the curved surface of the ingrown nail by an adhesive, followed by elevating the temperature to a predetermined level or higher to thereby effect flattening of the plate, so as to correct the ingrown nail by the restoring force exerted by the plate made of a shape memory metal or a resin. Further, Patent Document 3 discloses an apparatus for correcting a deformed nail, and a method for correcting a deformed nail using the apparatus. More specifically, the apparatus disclosed in Patent Document 3 comprises wires each having a hooked end portion for holding a lateral side portion of an ingrown nail. In use of this apparatus, the lateral side portions of an ingrown nail are held by the respective hooked end portions of the wires, and the lateral side portions of an ingrown nail are laterally pulled toward the center of the nail by the hooked end portions of the wires. More specifically, the apparatus of Patent Document 3 comprises: a first correcting body comprising a first engaging portion to be engaged with a lateral side portion of a nail, a first contacting portion to be contacted with a part of the surface of a nail, and a first connecting hook portion, wherein the first contacting portion extends between and connects to each other the first engaging portion and the first connecting hook portion; a second correcting body comprising a second engaging portion to be engaged with the other lateral side portion of a nail, a second contacting portion to be contacted with a part of the surface of a nail, and a second connecting hook portion, wherein the second connecting portion extends between and connects to each other the second engaging portion and the second connecting hook portion; and a correcting operation portion which is engaged with both of the first connecting hook portion and the second connecting hook portion so that the first engaging portion and said second engaging portion are kept to be laterally pulled toward the center of the nail with a predetermined pulling force, thereby pulling upward the lateral side portions of the nail.

However, with respect to the apparatus described in Patent Document 1, it is difficult to satisfactorily correct an ingrown nail for the following reason. In the nail correcting operation using this apparatus, the force sustained by the lateral side portions of the nail is larger in the lateral direction toward the center of the nail than in an upward direction. Therefore, it is difficult to obtain a satisfactory correcting effect. Further, the correction of an ingrown nail by using this apparatus takes a very long time extending over a few or several months. Since each of the post members of this apparatus has an upstanding portion, which renders this apparatus bulky, an ingrown nail patient who has this apparatus fitted thereon is forced to live a very cumbersome and inconvenient life for such a long period of time. Thus, the apparatus described in Patent Document 1 is impractical. The method described in Patent Document 2 has the following problem. In this method, a plate made of a shape memory metal or a resin is bent into a curvature and fittedly adhered to the curved surface of the ingrown nail by an adhesive, followed by effecting flattening of the curved plate. In such case, the nail surface cannot follow the flattening of the plate, resulting in either that the plate is likely to come off from the nail surface (when the adhesion strength is low) or that the flattening of the curved plate is likely to be prevented (when the adhesion strength is high). In addition, the ingrown nail correction using this method takes a very long time extending over a few or several months, throughout which the correcting device remains fitted on the nail of the patient. Thus, this method is very cumbersome and inconvenient to the patient.

Also in the case of the method described in Patent Document 3, the ingrown nail correction takes a very long time extending over a few or several months, throughout which the correcting device remains fitted on the nail of the patient, as in the case of the method described in Patent Document 2. Thus, this method is also very cumbersome and inconvenient to the patient. This method has another problem in that, since the lateral side portions of an ingrown nail are held and pulled by the respective hooked end portions of the wires, pain and/or bleeding frequently occurs, thus increasing the burden on the patient. In addition, this method has a defect in that this method cannot be applied when the nail to be corrected is too hard or too fragile or has tinea unguium.

The method (using a correction reagent) described in Patent Document 4 is as follows. Patent Document 4 discloses a correction reagent for correcting a deformed nail, comprising at least one reducing agent selected from the group consisting of cysteine, thioglycolic acid and thioglycolate. The invention of Patent Document 4 is based on the application of permanent waving technology for hair to the correction of a deformed nail, wherein the application was conceived in view of the fact that the composition of a nail is similar to that of hair. More specifically, the method of Patent Document 4 is performed as follows. An emulsifier is added to the above-mentioned reducing agent (which is a main component of a first agent for use in permanent waving) so as to obtain a cream-like agent having a reducing agent content of 5% by weight. This cream-like agent is used as an agent for correcting a deformed nail. First, a deformed nail (such as an ingrown nail) is allowed to grow forward until it has a forward free end portion (not in contact with the nail bed) having a satisfactory length in the forward direction. Next, a few through-apertures are formed in the forward free end portion of the nail. Then, the above-obtained cream-like agent is applied to the entire outer surface of the nail and allowed to stand for about 30 minutes. By this treatment, the disulfide bonds of the keratin protein of the nail are cleaved to form two mercapto groups per disulfide bond, thereby softening the nail. After the treatment, the cream-like agent is washed away with warm water. The thus softened deformed nail is manually corrected into an appropriate shape. A cold-setting resin is applied to the outer surface of the resultant corrected nail so as to fill the apertures formed in the forward free end portion of the nail, thereby fixing the shape of the corrected nail, and the thus treated nail is allowed to stand for 1 hour. Thereafter, the cold-setting resin is removed from the nail. The correction method described hereinabove has defects in that, since the operation is performed manually, the method is cumbersome and needs a high skill. Also, this correction method poses the following problem. In this method, the deformed nail has to be fully grown so as to provide a forward free end portion having a length sufficient for the above-described resin fixation operation after the manual correction of the nail. However, in many or most cases, an ingrown nail patient has an ingrown nail cut to the quick; therefore, the correction of the ingrown nail cannot be performed until the ingrown nail has fully grown. Thus, this correction method is disadvantageous in that very frequently, this correction method cannot be performed immediately after an ingrown nail patient has decided to undergo a nail correction using this method.

It should be noted that the correction reagent used in the method described in Patent Document 4 cannot be used in combination with any of the conventional correcting devices or apparatuses (for example, the correcting devices or apparatuses disclosed in Patent Documents 1 to 3). The reason for this is as follows. The conventional correcting devices or apparatuses are premised on that they are used for correcting a nail in the ordinary state, that is, a stiff and hard nail (i.e., a non-softened nail). Therefore, if any of the conventional correcting devices or apparatuses are used on an ingrown nail in the softened state, the softened nail sustains too great a deforming stress (such as a buckling stress), so that the softened nail will suffer a drastic deformation, such as a drastic buckling. As a result, the desired correction of an ingrown nail cannot be attained at all. Especially, in the case where the correction reagent used in the method described in Patent Document 4 is used in combination with any of the correcting apparatus described in Patent Document 1 and the correcting device described in Patent Document 3, the force sustained by the lateral side portions of the nail is larger in the lateral direction toward the center of the nail than in an upward direction. Thus, it is very difficult for any of these correcting apparatus and correcting device to be used for correcting an ingrown nail in the softened state into a desired shape. Further, especially when the correcting device described in Patent Document 3 is used for correcting an ingrown nail in the softened state, the lateral pulling force (toward the center of the nail) is locally exerted only on the lateral side portions of the nail with which the hooked end portions of the wires are engaged, thus rendering it substantially impossible to correct the ingrown nail into a desired shape. Further, even when the correction reagent used in the method described in Patent Document 4 is actually used in combination with any of the conventional correcting devices or apparatuses despite the disadvantages caused by the correction reagent, the above-mentioned problems accompanying the use of the conventional correcting devices or apparatuses remain unsolved, and substantially the same problems occur. For example, even when the correction reagent used in the method described in Patent Document 4 is actually used in combination with the method described in Patent Document 2 (employing a plate made of a shape memory metal or resin), there occurs a problem in that the plate is likely to easily come off from the nail surface.

Patent Document 1: U.S. Pat. No. 4,057,055.
Patent Document 2: Unexamined Japanese Patent Application Laid-Open Specification No. Hei 8-215227.
Patent Document 3: Unexamined Japanese Patent Application Laid-Open Specification No. 2001-276104.
Patent Document 4: Unexamined Japanese Patent Application Laid-Open Specification No. 2004-238288.

DISCLOSURE OF THE INVENTION

Problems to be Solved by the Invention

Therefore, it has been desired to develop a technology for correcting an ingrown nail, which is advantageous not only in that an ingrown nail can be corrected surely, easily and within a very short time, but also in that there is caused no burden or no pain to an ingrown nail patient, and that correction of an ingrown nail can be performed at any time, irrespective of whether or not the ingrown nail has fully grown forward.

Means to Solve the Problems

In this situation, the present inventor has made extensive and intensive studies with a view toward solving the above-mentioned problems. As a result, he has unexpectedly found that the above-mentioned problems can be solved by an apparatus for correcting an ingrown nail by lifting a nail edge grown into a nail bed, which comprises: an upstanding push-down member having at a lower end thereof a push-down head; a laterally extending, lifting angle maintenance means which is secured, at a middle portion thereof, to the upstanding push-down member; and a pair of lifting members extending downwardly from respective portions of the lifting angle maintenance means, which portions are opposite relative to the middle portion of the lifting angle maintenance means at which the upstanding push-down member is secured, each lifting member having an anchor at a lower end thereof, wherein, in use of the apparatus, when the lifting members are placed under tension, the anchors which are, respectively, secured to side portions of the outer surface of the nail are lifted to thereby exert an ingrown nail-correcting, lifting force on each of the side portions of the outer surface of the nail while causing the upstanding push-down member to push the middle portion of the outer surface of the nail in the thicknesswise direction of the nail. It has also been found that, when the ingrown nail correction using the above-mentioned apparatus is performed after the nail has been softened using a nail softening agent (e.g., the reducing agent for cleaving disulfide bonds, as described in Patent Document 4), the ingrown nail correction can be effected surely and within a very short period. The present invention has been completed, based on these findings.

The foregoing and other objects, features and advantages of the present invention will be apparent from the following detailed description taken in connection with the accompanying drawings and the appended claims.

Effects of the Invention

By the use of the apparatus of the present invention, an ingrown nail can be surely corrected within a very short time, e.g., within about 30 minutes to about 1 hour, with a very simple operation and without causing pain to a patient. Therefore, the apparatus of the present invention is very effective and, hence, has a very high practicality.

DESCRIPTION OF REFERENCE NUMERALS

Figure 1:
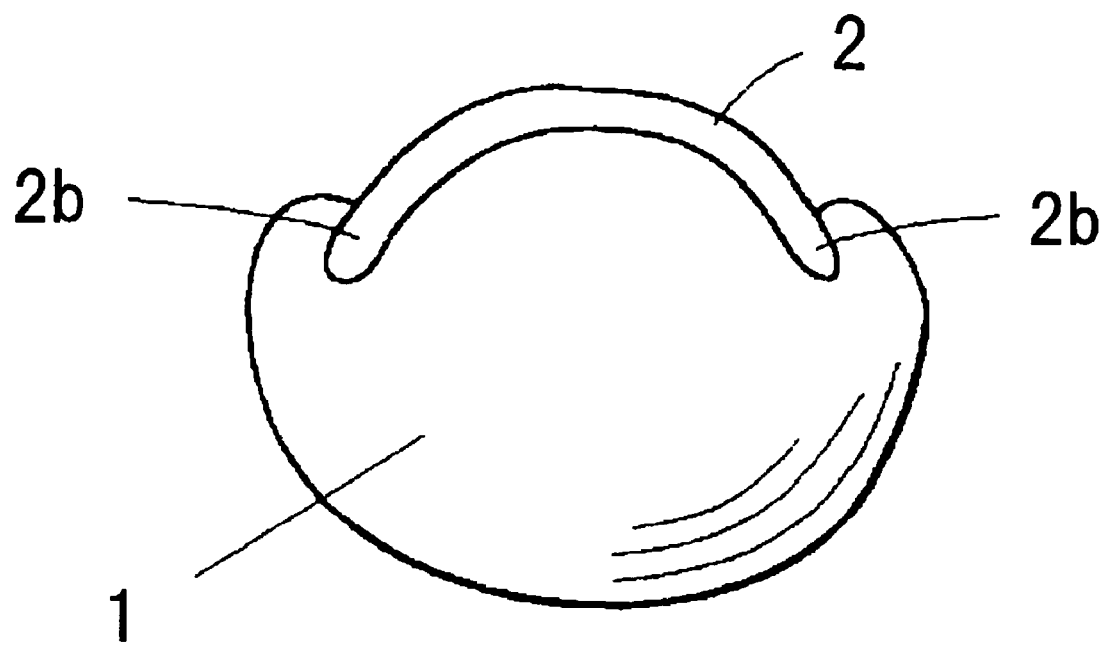
FIG. 1 is a front view showing a first toe having an ingrown nail, as view from the tip of the first toe.

A: Angle of lifting member 5, relative to the vertical direction as indicated by a broken line (the vertical direction being defined as the thicknesswise direction of the finger having the nail)
1: First toe having an ingrown nail
2: Ingrown nail
2a: Side portion of an ingrown nail
2b: Ingrown part of a side portion of an ingrown nail
3: Upstanding push-down member
3a: Push-down head of an upstanding push-down member
3b: Rod-like top portion of an upstanding push-down member
3c: Threaded main body of an upstanding push-down member
3d: Height adjustment cross handle of an upstanding push-down member
4: Lifting angle maintenance means
4a: Guiding through-hole
4b: Slit for securing a lifting member
4c: Main body (having movable wings) of a lifting angle maintenance means
4d: Movable wing
4e: Plate for securing a lifting member
5: Lifting member
5a: Supplemental lifting member
6: Anchor
6a: Supplemental anchor
7: Nut means
8: Helical compression spring means
8a: Nut for securing a helical compression spring means
9: Lifting member-securing central rod
10a: External screw for securing an upstanding push-down member
10b: External screw for securing a lifting member
11: Resilient, lifting angle maintenance means, which serves also as a lifting member

BEST MODE FOR CARRYING OUT THE INVENTION

According to the present invention, there is provided an apparatus for correcting an ingrown nail by lifting a nail edge grown into a nail bed, which comprises:

an upstanding push-down member having at a lower end thereof a push-down head;

a laterally extending, lifting angle maintenance means which is secured, at a middle portion thereof, to the upstanding push-down member; and a pair of lifting members extending downwardly from respective portions of the lifting angle maintenance means, which portions are opposite relative to the middle portion of the lifting angle maintenance means at which the upstanding push-down member is secured, each lifting member having an anchor at a lower end thereof, wherein, in use of the apparatus:

the apparatus is installed on the outer surface of a nail in a manner such that the push-down head of the upstanding push-down member contacts a middle portion of the outer surface of the nail, and that the anchors of the lifting members are, respectively, secured to the outer surface of the nail at side portions thereof which are opposite relative to the middle portion at which the push-down head of the upstanding push-down member contacts the outer surface of the nail, as viewed from the tip of a finger having the nail, and when the lifting members are placed under tension, the anchors are lifted to thereby exert an ingrown nail-correcting, lifting force on each of the side portions of the outer surface of the nail while causing the upstanding push-down member to push the middle portion of the outer surface of the nail in the thicknesswise direction of the nail.

For easier understanding of the present invention, the essential features and various preferred embodiments of the present invention are enumerated below.

1. An apparatus for correcting an ingrown nail by lifting a nail edge grown into a nail bed, which comprises:

an upstanding push-down member having at a lower end thereof a push-down head;

a laterally extending, lifting angle maintenance means which is secured, at a middle portion thereof, to the upstanding push-down member; and a pair of lifting members extending downwardly from respective portions of the lifting angle maintenance means, which portions are opposite relative to the middle portion of the lifting angle maintenance means at which the upstanding push-down member is secured, each lifting member having an anchor at a lower end thereof, wherein, in use of the apparatus:

the apparatus is installed on the outer surface of a nail in a manner such that the push-down head of the upstanding push-down member contacts a middle portion of the outer surface of the nail, and that the anchors of the lifting members are, respectively, secured to the outer surface of the nail at side portions thereof which are opposite relative to the middle portion at which the push-down head of the upstanding push-down member contacts the outer surface of the nail, as viewed from the tip of a finger having the nail, and when the lifting members are placed under tension, the anchors are lifted to thereby exert an ingrown nail-correcting, lifting force on each of the side portions of the outer surface of the nail while causing the upstanding push-down member to push the middle portion of the outer surface of the nail in the thicknesswise direction of the nail.

2. The apparatus according to item 1 above, wherein, when the apparatus is installed on the outer surface of a nail, each of the lifting members extends downwardly from the lifting angle maintenance means in a vertical direction or a direction inclined toward the longitudinal central axis of the nail, wherein the vertical direction is defined as the thicknesswise direction of the finger having the nail.

3. The apparatus according to item 2 above, wherein, when each of the lifting members extends down-wardly from the lifting angle maintenance means in a direction inclined toward the longitudinal axis of the nail, the inclination angle is at least 10° relative to the vertical direction, as measured at the connection point between the lifting member and the anchor.

4. The apparatus according to item 3 above, wherein the inclination angle is at least 20° relative to the vertical direction.

5. The apparatus according to any one of items 1 to 4 above, wherein the lifting interval is 1 or more in terms of a ratio of the distance between the lifting members as measured at positions of contacts between the lifting members and the lifting angle maintenance means, relative to the width of the nail on which the apparatus is installed.

6. The apparatus according to item 5 above, wherein the lifting interval is 1.2 or more.

7. The apparatus according to any one of items 1 to 6 above, wherein each of the lifting members is independently selected from the group consisting of a flexible linear body and a flexible rod.

8. The apparatus according to any one of items 1 to 7 above, wherein the lifting members are secured to the upstanding push-down member or the lifting angle maintenance means.

9. The apparatus according to any one of items 1 to 8 above, wherein the lifting angle maintenance means has guiding through-holes for respectively receiving therethrough the lifting members.

10. The apparatus according to item 9 above, wherein the lifting members are, respectively, inserted in the guiding through-holes of the lifting angle maintenance means and engaged with the peripheries of the guiding through-holes, thereby securing the lifting members to the lifting angle maintenance means.

11. The apparatus according to any one of items 1 to 10 above, wherein:

the upstanding push-down member has a shape selected from the group consisting of a vertically extending rod-like shape and a plate-like shape which has both surfaces thereof extending vertically and along the longitudinal direction of the finger having the nail on which the apparatus is installed, and the lifting angle maintenance means has a shape selected from the group consisting of a horizontally extending rod-like shape, an inverted U or V-like shape, a U or V-like shape, and a plate-like shape which has both surfaces thereof extending horizontally.

12. The apparatus according to any one of items 1 to 11 above, which further comprises a lifting force adjusting means which is secured to the upstanding push-down member and the lifting members, wherein, in use of the apparatus, the lifting force adjusting means is operated to change the vertical positions of the lifting members relative to the push-down head of the upstanding push-down member, thereby adjusting the lifting forces of the lifting members.

13. The apparatus according to item 12 above, wherein the lifting force adjusting means comprises a nut means, a helical compression spring means and a lifting member-securing central rod extending horizontally which are disposed on each other in this order, to thereby form a 'nut/spring/rod' vertical stack, the lifting member-securing central rod having both ends thereof which are, respectively, secured to the upper ends of the lifting members, the lifting member-securing central rod having a thicknesswise extending through-hole at its center portion of the length thereof, wherein the upstanding push-down member has a vertically extending rod-like shape and has a threaded top portion which is movably screw-wise inserted into and through the nut means and movably non-screw-wise inserted into and through the helical compression spring means and the through-hole of the lifting member-securing central rod, thereby proving a structure in which the threaded top portion of the upstanding push-down member is vertically inserted into and through the 'nut/spring/rod' vertical stack, wherein, in use of the apparatus, the 'nut/spring/rod' vertical stack is caused to serve as the lifting force adjusting means by screw-wise turning the nut means in either direction to move the position of the nut means upward or downward, thereby moving the position of the lifting member-securing central rod upward or downward through the helical compression spring means functioning as a mechanical cushion between the nut means and the lifting member-securing central rod.

14. The apparatus according to any one of items 1 to 13 above, which further comprises a pair of supplemental lifting members extending downwardly from respective portions of the lifting angle maintenance means, which portions are closer to the upstanding push-down member than the lifting members, each supplemental lifting member having a supplemental anchor at a lower end thereof.

15. Use of the apparatus of any one of items 1 to 14 above in correction of an ingrown nail which is softened by a nail softening agent comprising a protein degrading substance.

16. An apparatus for correcting an ingrown nail by lifting a nail edge grown into a nail bed, which comprises:

an upstanding push-down member having at a lower end thereof a push-down head;

a laterally extending, resilient, lifting angle maintenance means which is secured, at a middle portion thereof, to the upstanding push-down member; and a pair of anchors which are respectively secured to the lower surface of the lifting angle maintenance means at portions thereof which are opposite relative to the middle portion of the lifting angle maintenance means at which the upstanding push-down member is secured, wherein, in use of the apparatus:

the apparatus is installed on an outer surface of a nail in a manner such that the push-down head of the upstanding push-down member contacts a middle portion of the outer surface of the nail, that opposing end portions of the resilient, lifting angle maintenance means are bent downward to bring the anchors into contact with the outer surface of the nail at side portions thereof which are opposite relative to the middle portion at which the push-down head of the upstanding push-down member contacts the outer surface of the nail, as viewed from the tip of a finger having the nail, and that the anchors are, respectively, secured to the side portions of the outer surface of the nail, to thereby lift the anchors under resilient tension caused by the bent lifting angle maintenance means to exert an ingrown nail-correcting, lifting force on each of the side portions of the outer surface of the nail while causing the upstanding push-down member to push the middle portion of the outer surface of the nail in the thicknesswise direction of the nail.

17. Use of the apparatus of item 16 above in correction of an ingrown nail which is softened by a nail softening agent comprising a protein degrading substance.

Hereinbelow, the present invention is described in detail with reference to the accompanying drawings.

FIG. 1 is a front view showing first toe 1 having ingrown nail 2, as view from the tip of first toe 1. An ingrown nail (onychocryptosis) is generally also known as a "pincer nail". As shown in FIG. 1, an ingrown nail is a nail disease where one or both side portions 2b of nail 2 grow or cut into one or both side portions of the nail bed, thus causing a pain which may sometimes be very acute.

The apparatus of the present invention is employed to correct ingrown nail 2 by lifting both side portions of the outer surface of ingrown nail 2 while pushing down the middle portion of the outer surface of ingrown nail 2. The apparatus of the present invention is described below in detail with reference to FIGS. 2 and 3.

Figure 2:
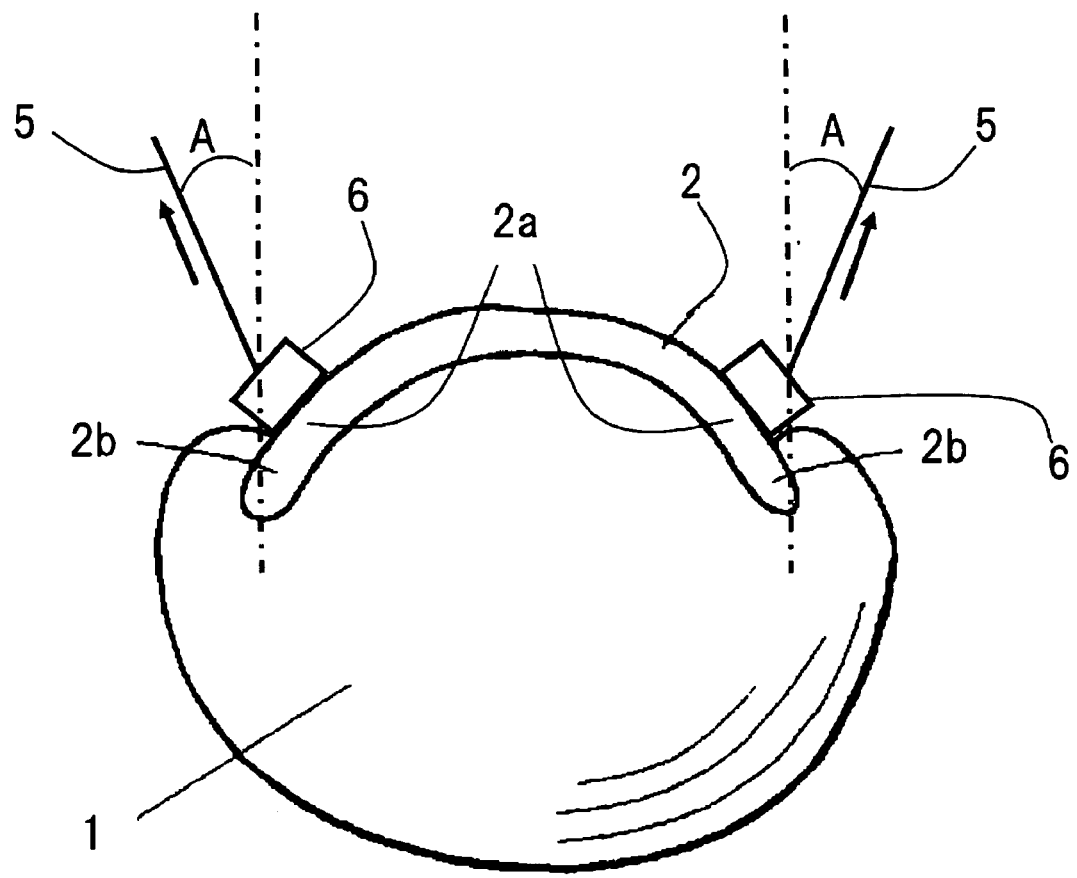
FIG. 2 is an explanatory view concerning the angle at which each of the lifting members of the apparatus of the present invention is secured to the outer surface of the nail.
Figure 3:
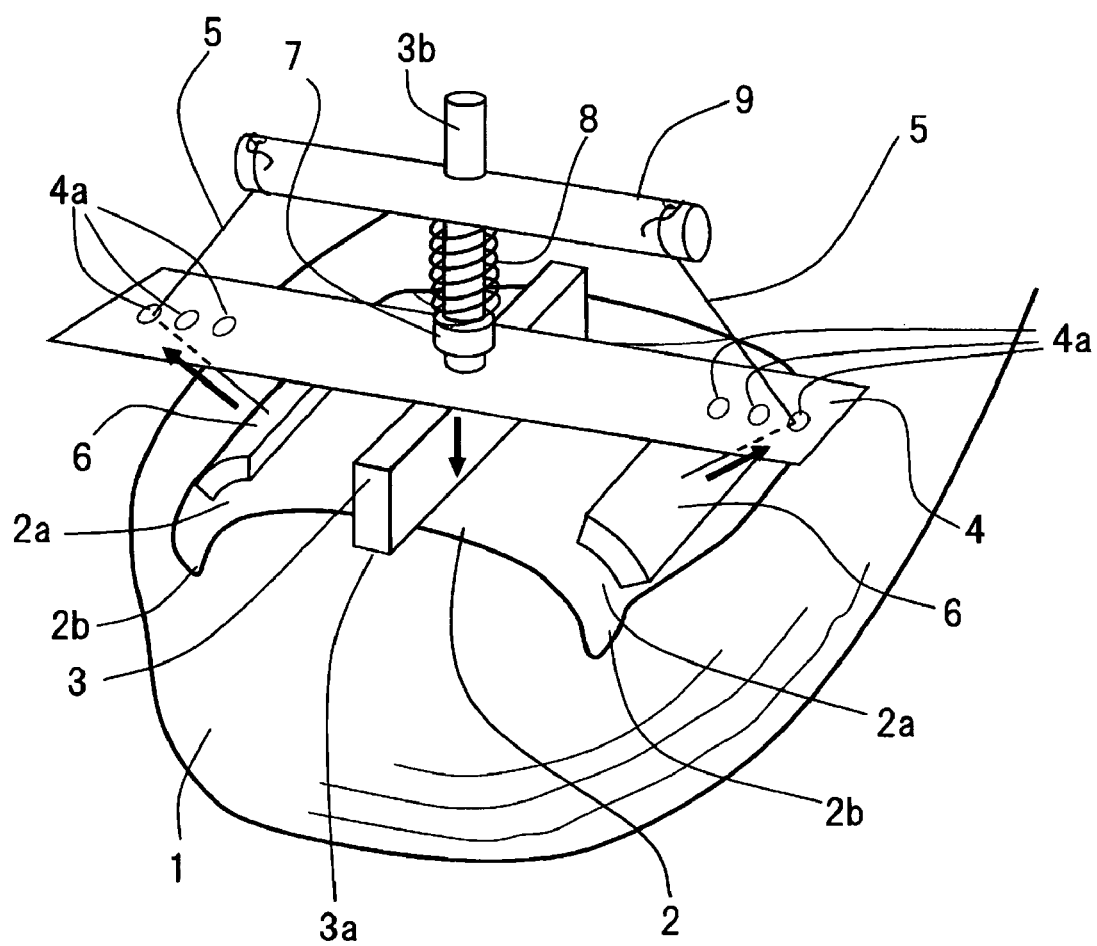
FIG. 3 is a perspective view of an embodiment of the apparatus of the present invention, which is installed on the outer surface of a first toe having an ingrown nail.

FIG. 2 is an explanatory view concerning the angle at which each of the lifting members of the apparatus of the present invention is secured to the outer surface of the nail. FIG. 3 is a perspective view of an embodiment of the apparatus of the present invention, which is installed on the outer surface of a first toe having an ingrown nail. As shown in FIG. 3, the apparatus of the present invention comprises:

upstanding push-down member 3 having at a lower end thereof push-down head 3a;

laterally extending, lifting angle maintenance means 4 which is secured, at a middle portion thereof, to upstanding push-down member 3; and a pair of lifting members 5,5 extending downwardly from respective portions of lifting angle maintenance means 4, which portions are opposite relative to the middle portion of lifting angle maintenance means 4 at which upstanding push-down member 3 is secured, each lifting member 5 having anchor 6 at a lower end thereof.

The apparatus of the present invention is used as follows. First, the apparatus is installed on the outer surface of nail 2 in a manner such that push-down head 3a of upstanding push-down member 3 contacts a middle portion of the outer surface of nail 2, and that anchors 6,6 of lifting members 5,5 are, respectively, secured to the outer surface of nail 2 at side portions 2a,2a thereof which are opposite relative to the middle portion at which push-down head 3a of upstanding push-down member 3 contacts the outer surface of nail 2, as viewed from the tip of finger 1 having nail 2. For performing correction of ingrown nail 2, lifting members 5,5 are placed under tension to cause anchors 6,6 to be lifted to thereby exert an ingrown nail-correcting, lifting force on each of side portions 2a,2a of the outer surface of nail 2 while causing push-down head 3a of upstanding push-down member 3 to push the middle portion of the outer surface of nail 2 in the thicknesswise direction of nail 2.

In the present invention, it is preferred that, when the apparatus is installed on the outer surface of nail 2, each of lifting members 5,5 extends downwardly from lifting angle maintenance means 4 in a vertical direction or a direction inclined toward the longitudinal central axis of nail 2. The vertical direction is defined as the thicknesswise direction of the finger having the nail. Further, when each of lifting members 5,5 extends downwardly from lifting angle maintenance means 4 in a direction inclined toward the longitudinal axis of nail 2, an appropriate inclination angle ("A" shown in FIG. 2) relative to the vertical direction, as measured at the connection point between lifting member 5 and anchor 6, varies depending on the degree of curvature of and the hardness of the ingrown nail, etc. However, it is preferred that the inclination angle A is at least 10°, more advantageously at least 20° relative to the vertical direction, as measured at the connection point between lifting member 5 and anchor 6. Depending on the condition of the ingrown nail (for example, when the nail curvature is relatively large), too small a value of the above-mentioned the inclination angle A may result in unsatisfactory correction such that the nail is bent like a hinge where the longitudinal central axis of the nail serves as a fulcrum, thus flattening only the curvature of the middle portion of the nail while leaving the curvature of the ingrown side portions of the nail uncorrected or insufficiently corrected. For preventing such problem, it is preferred that the inclination angle A is much larger than the above-mentioned preferred value (for example, at least 50°).

With respect to the upper limit value of the inclination angle A, there is no particular limitation as long as there can be exerted a lifting force necessary for correcting an ingrown nail. However, in general, it is preferred that the inclination angle A is not more than 90°, more advantageously not more than 85°, still more advantageously not more than 80°. In the present invention, the inclination angle A is as measured after the installation of the apparatus of the present invention on ingrown nail 2 and before the commencement of the nail correcting operation by placing lifting members 5,5 under tension.

Figure 7:
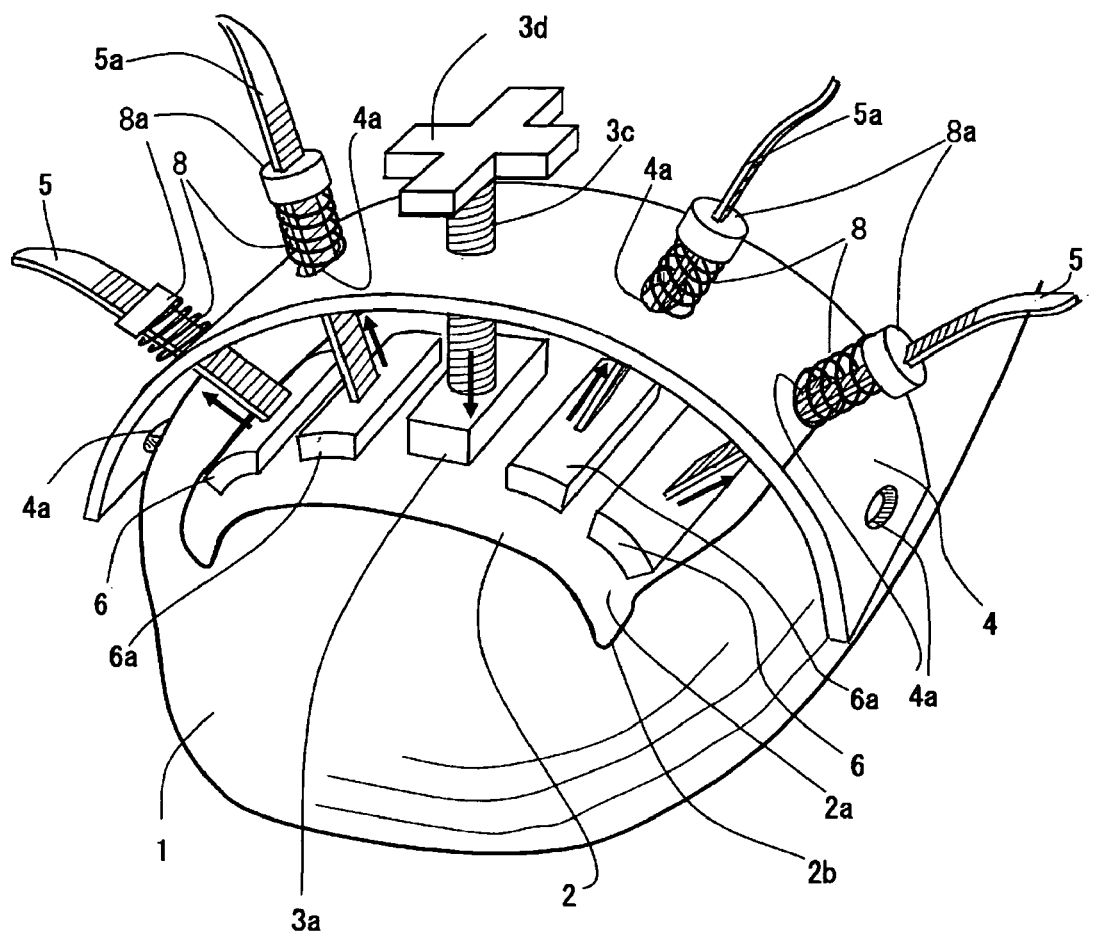
FIG. 7 is a perspective view of still a further embodiment of the apparatus of the present invention, which is installed on the outer surface of a first toe having an ingrown nail.
Figure 8:
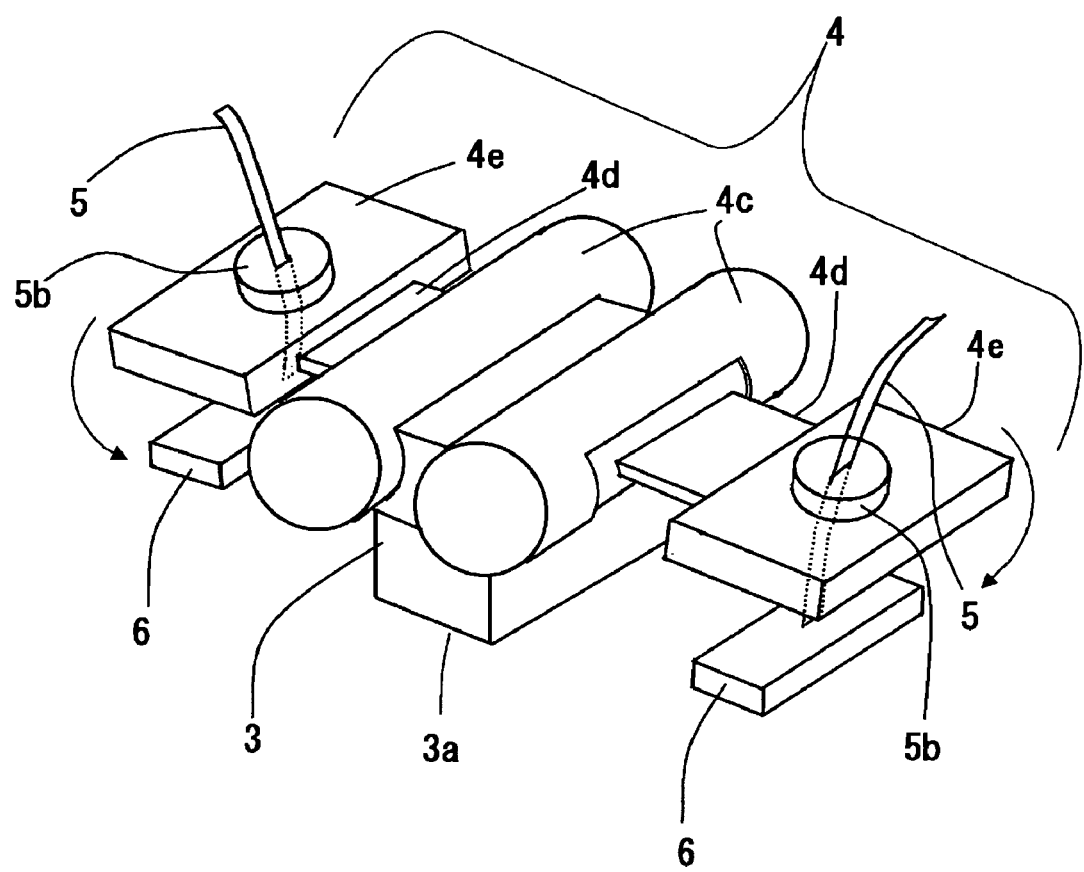
FIG. 8 is a perspective view of still a further embodiment of the apparatus of the present invention.

In FIGS. 2, 3 and 7, the arrows indicate either the direction of the tensile force exerted by lifting members 5,5 or the direction of the push-down force exerted by upstanding push-down member 3. In FIG. 8, the arrows indicate the movable directions of movable wings 4d,4d of lifting angle maintenance means 4.

In the present specification, as mentioned above, the "vertical direction" is defined as the thicknesswise direction of finger 1. In other words, when finger 1 is placed on a plain so that the outer surface of nail 2 faces upward, the "vertical direction" defined herein is a direction perpendicular to the above-mentioned plain, as viewed from the tip of a finger having the nail.

The inclination angle A is adjusted in accordance with the size of the ingrown nail to be corrected by the apparatus of the present invention. The adjustment of the inclination angle A can be performed, for example, by changing a ratio of the distance between lifting members 5,5, the distance being as measured at the positions of contacts between lifting members 5,5 and the bottom surface of lifting angle maintenance means 4, relative to the width of the nail on which the apparatus is installed (hereinafter, the ratio is frequently referred to as "lifting interval"). (For example, in FIG. 3, the above-mentioned distance between lifting members 5,5 is the distance between guiding through-holes 4a,4a which respectively receive therethrough lifting members 5,5.) (When there is no direct contact between and lifting members 5,5 and lifting angle maintenance means 4, the above-mentioned distance between lifting members 5,5 is as measured between the positions of intersection between lifting members 5,5 and the bottom surface of lifting angle maintenance means 4, as viewed from the tip of the nail.) For example, as shown in FIGS. 3 and 7, the above-mentioned lifting interval can be rendered easily adjustable by a method in which lifting angle maintenance means 4 is prepared so that a plurality of pairs of guiding through-holes 4a,4a are provided at different distances from upstanding push-down member 3. The distance between guiding through-holes 4a,4a is changed in accordance with the desired lifting interval. The lifting interval is preferably 1 or more, more preferably 1.2 or more, still more preferably 1.4 or more. With respect to the number of guiding through-holes 4a,4a and to the distance between the adjacent guiding through-holes 4a,4a (in terms of the distance between the centers of the adjacent guiding through-holes 4a,4a), there is no particular limitation. However, the number of guiding through-holes 4a,4a is preferably in the range of from 4 to 30, more preferably in the range of from 6 to 20, still more preferably in the range of from 8 to 14. The distance between the adjacent guiding through-holes 4a,4a is preferably in the range of from 3 to 20 mm, more preferably in the range of from 4 to 15 mm, still more preferably in the range of from 5 to 10 mm. Needless to say, it is possible to use a method in which there are provided a plurality of lifting angle maintenance means 4,4 which are different in the distance between the adjacent guiding through-holes 4a,4a, and a suitable lifting angle maintenance means 4 is selected in accordance with the size of the ingrown nail to be corrected. In the case of an embodiment where lifting angle maintenance means 4 does not have guiding through-hole 4a, the contact positions between lifting members 5,5 and lifting angle maintenance means 4 are considered as guiding through-holes 4a,4a. For example, assume an embodiment where lifting members 5,5 respectively have hooks at their upper ends; lifting angle maintenance means 4 has hooks at its positions at which to contact lifting members 5,5; and the hooks of lifting members 5,5 are engaged with the hooks of lifting angle maintenance means 4. In this embodiment, the hooks of lifting angle maintenance means 4 are considered as guiding through-holes 4a,4a, in connection with the adjustment of the inclination angle A.

If the above-mentioned tension is the same, when the angle (hereinafter referred to as the "tension-nail angle") of the direction of the tension is perpendicular to a flat surface of the nail to which the tension is applied (or when the tension-nail angle is normal to a curved surface of the nail to which the tension is applied), the tension applied to the nail becomes maximum. Therefore, it is preferred that the tension-nail angle is perpendicular (or normal). The tension-nail angle can be adjusted by changing the lifting interval. The value of lifting interval necessary for obtaining a tension-nail angle which is perpendicular, varies depending not only on the size and curvature of the nail but also on the degree of corrective shape change of the nail, attained using the apparatus of the present invention. Therefore, it is possible to employ a measure that during the correction of an ingrown nail by using the apparatus of the present invention, the lifting interval is gradually changed in accordance with the corrective shape change of the nail so as to maintain a tension-nail angle which is perpendicular. However, in general, a desired corrective effect on the nail can be achieved without employing such measure, as long as the tension-nail angle is perpendicular before the tension is applied or the tension-nail angle becomes perpendicular during the progress of a corrective shape change of the nail by using the apparatus of the present invention. In many cases, when the inclination angle A is set at about 45°, the tension-nail angle becomes about perpendicular. In this respect, the inclination angle A is preferably 30 to 60°, more preferably 40 to 50°.

An appropriate size of the nail varies depending on which the type of the nail (i.e., a finger nail, a toe nail, a thumb nail, a little finger nail, etc.) and the patient. However, the width of the nail is generally less than 3 cm, the apparatus of the present invention may have a construction such that the distance between the lifting members 5,5 is fixed at a value of 3 cm or more so that the inclination angle A can be maintained at around a specific value, irrespective of the size of the nail to be corrected. In this case, the lifting interval, i.e., the distance as measured between the positions of contacts between lifting members 5,5 and the bottom surface of lifting angle maintenance means 4, is preferably 3 to 10 cm, more preferably 3.5 to 8 cm, still more preferably 4 to 5.5 cm. (When there is no direct contact between and lifting members 5,5 and lifting angle maintenance means 4, the lifting interval is as measured between the positions of intersection between lifting members 5,5 and the bottom surface of lifting angle maintenance means 4, as viewed from the tip of the nail.)

By placing lifting members 5,5 under tension, an ingrown nail-correcting, lifting force is exerted on each of side portions 2a,2a of the outer surface of ingrown nail 2 while causing upstanding push-down member 3 to push the middle portion (positioned between anchors 6,6) of the outer surface of ingrown nail 2 in the thicknesswise direction of ingrown nail 2. In FIG. 3, upstanding push-down member 3 has a plate-like shape which has both surfaces thereof extending vertically and along the longitudinal direction of the finger having the nail. Alternatively, upstanding push-down member 3 may have a vertically extending rod-like shape. However, for performing an effective correction of an ingrown nail, it is desired that at least the lower end portion (including push-down head 3a) of upstanding push-down member 3 has a shape which is suitable for pushing down the middle portion of the outer surface of ingrown nail 2 over a relatively large length in the longitudinal direction of the finger, such as the above-mentioned plate-like shape. In such case, at least the lower end portion (including push-down head 3a) of upstanding push-down member 3 may have a shape such that the above-mentioned relatively large length in the middle portion of the outer surface of ingrown nail 2 in the longitudinal direction of the finger extends at intervals. An example of such shape include a shape which is made by disposing, horizontally at intervals in a line, a plurality of vertically extending rods so that the respective lower ends thereof are horizontally arranged at intervals in a line. The lower end portion (including push-down head 3a) of upstanding push-down member 3 may have a shape made by disposing a plurality of thin plates in parallel at intervals. The material for upstanding push-down member 3 is not particularly limited and can be selected from various metals and resins. However, it is desired that at least push-down head 3a (which are to be contacted with a nail) of upstanding push-down member 3 is made of a material which does not damage a nail. Examples of materials for push-down head 3a of upstanding push-down member 3 include elastic bodies, such as a rubber. However, push-down head 3a of upstanding push-down member 3 may be made of a hard material, such as a hard resin or a metal, as long as push-down head 3a is smooth and is shaped so as not to damage a nail. It is preferred that push-down head 3a has its lower end (which is to be contacted with a nail) shaped so as to fit the curvature of a nail, more advantageously to fit the correct curvature of a nail which is desired to be obtained after the correction of an ingrown nail.

With respect to push-down head 3a, it is possible to take a measure that a few types of push-down head 3a, which are different in width, are prepared, and during the correction of an ingrown nail, the few types of push-down head 3a are appropriately switched from one to another in accordance with the progress of the correction, thereby increasing the corrective effect. This measure is explained below. During the nail correction by using the apparatus of the present invention, the side portions of a nail are bent over upward, and most suitable positions of the bending fulcrums are gradually changed in accordance with the progress of the correction. The bending fulcrums can be set at desired, most suitable positions by changing the width of push-down head 3a. The smaller the width of push-down head 3a, the smaller the distance of the bending fulcrums from the middle portion of the outer surface of the nail. In other words, the greater the width of push-down head 3a, the greater the distance of the bending fulcrums from the middle portion of the outer surface of the nail. During the nail correction by using the apparatus of the present invention, push-down head 3a is changed based on the observation of the corrective shape change of the nail so as to maintain the width of push-down head 3a at a value which can achieve a maximum effect of correction.

With respect to the dimensions of push-down member 3, there is no particular limitation. However, it is preferred that push-down member 3 has the following dimensions. The length of push-down member 3 (as measured at push-down head 3a) is preferably 0.5 to 8.0 cm, more preferably 1 to 5.0 cm, still more preferably 1.5 to 3.0 cm. The width of push-down member 3 (as measured at push-down head 3a) is preferably 0.1 to 1.5 cm, more preferably 0.2 to 1.2 cm, still more preferably 0.3 to 1.0 cm.

With respect to lifting angle maintenance means 4, there is no particular limitation as long as the inclination angle A mentioned above can be maintained at a desired value. For example, lifting angle maintenance means 4 may have a plate-like shape which has both surfaces thereof extending horizontally as shown in FIG. 3 or any other shape, such as a shape selected from the group consisting of a horizontally extending rod-like shape, an inverted U or V-like shape, and a U or V-like shape. In general, it is preferred that lifting angle maintenance means 4 has an inverted U-like shape (as shown in FIG. 7), which generally corresponds to the curvature of a nail as shown in FIG. 7. Also, as shown in FIG. 8, lifting angle maintenance means 4 may have a structure in which the lifting members are attached to movable wings which render adjustable both the inclination angle A and the lifting interval. With respect to the material for lifting angle maintenance means 4, there is no particular limitation. The material for lifting angle maintenance means 4 can be selected from various metals and resins. With respect to the dimensions of lifting angle maintenance means 4, there is no particular limitation except that the lifting interval is desired to be in the above-mentioned preferred range.

In the case of lifting angle maintenance means 4 shown in any of FIGS. 3 to 8, the shape thereof as viewed from above is rectangular. However, with respect to the shape of lifting angle maintenance means 4, there is no particular limitation as long as a satisfactory lifting effect can be achieved. For example, the shape of lifting angle maintenance means 4, as viewed from above, may be any of a circle, an ellipse and a triangle.

In FIG. 3, each of lifting members 5,5 is independently selected from the group consisting of a flexible linear body and a flexible rod. Herein, a "linear body" means a linearly extending member having a diameter of 2 mm or less, and a "flexible rod" means a linearly extending member having a diameter of more than 2 mm. Any of the flexible linear body and the flexible rod may be made of any of a hard material and a flexible material. Examples of a flexible linear body and a flexible rod include a string of a resilient body, such as rubber, a string or rod of a resin, such as nylon, and a metallic wire. With respect to the length of a flexible linear body and a flexible rod, there is no particular limitation. However, the length is generally 0.5 to 10 cm, preferably 1.0 to 5.0 cm, more preferably 1.5 to 3.5 cm, in terms of the distance between the positions at which the flexible linear body or flexible rod is contacted with anchor 6 and lifting angle maintenance means 4.

Lifting members 5,5 are not limited to the above-mentioned flexible linear body and flexible rod. Various shapes, such as chains or belts, may be used. Further, as shown in FIGS. 7 and 8, in a preferred embodiment of the present invention, lifting members 5,5 are belt-like and have a securing function as in the case of the so-called "cable ties" or the like. The material for belt-like lifting members 5,5 having a securing function can be selected from hard materials, such as a metal or a hard plastic. However, from the viewpoint of, e.g., the ease in the installation of the apparatus to a nail, it is preferred that the material for belt-like lifting members 5,5 having a securing function is a flexible material, such as a soft plastic. In the case of belt-like lifting members 5,5 having a securing function, such lifting members 5,5 can be easily secured at arbitrary positions to lifting angle maintenance means 4. Further, such lifting members 5,5 can be easily produced from commercially available materials and, hence, are advantageous from the viewpoint of the production efficiency and cost reduction of the apparatus of the present invention.

Lifting members 5,5 are not limited to those exemplified above. Lifting members 5,5 are not particularly limited as long as there can be exerted an ingrown nail-correcting, lifting force, through anchors 6,6, on each of side portions 2a,2a of the outer surface of ingrown nail 2. For example, lifting members 5,5 are of a plate-like shape. Lifting members 5,5 may be different in material, shape and/or length.

Lifting members 5,5 have anchors 6,6 at respective lower ends thereof. In the use of the apparatus of the present invention, anchors 6,6 are, respectively, secured to side portions 2a,2a of the outer surface of ingrown nail 2. With respect to the shape of anchors 6,6, there is no particular limitation as long as a satisfactory adhesion area can be obtained between each of anchors 6,6 and the outer surface of ingrown nail 2. Anchors 6,6 may have a plate-like shape as shown in FIG. 3 or other shape. With respect to the material for anchors 6,6, there is no particular limitation. The material for anchors 6,6 can be selected from various resins and metals. However, from the viewpoint of ease of working, ease of adhesion to a nail, and cost reduction, it is preferred that anchors 6,6 are prepared from a resin foam, such as an acrylic foam or a urethane foam. With respect to the dimensions of anchors 6,6, there is no particular limitation. The dimensions of anchors 6,6 can be appropriately selected in accordance with, e.g., the size and hardness of ingrown nail 2. The preferred dimensions are as follows. The length of anchor 6 is preferably 0.3 to 3.5 cm, more preferably 0.5 to 3.0 cm, still more preferably 0.7 to 2.0 cm. The width of anchor 6 is preferably 0.2 to 1.5 cm, more preferably 0.3 to 1.0 cm, still more preferably 0.4 to 0.8 cm. Even when the ingrown nail to be corrected has a high hardness, an effective correction can be obtained, for example, by increasing the width of anchor 6, to thereby increase the area to which the ingrown nail-correcting lifting force is applied. In such case, for example, the width of anchor 6 is increased to about 30 to about 40% of the width of the nail to be corrected. The thickness of anchor 6 is preferably 0.2 to 2.0 cm, more preferably 0.5 to 1.5 cm, still more preferably 0.7 to 1.2 cm.

With respect to the adhesive used for adhering anchors 6,6 to the outer surface of the nail, a conventional adhesive may be used. However, it is necessary to use an adhesive which satisfies the requirement that, during the correction of the nail, anchors 6,6 are not easily detached from the outer surface of the nail and that, after the correction of the nail, anchors 6,6 can be easily detached from the outer surface of the nail. An example of a conventional adhesive is Aron Alpha (registered trademark)(manufactured and sold by TOAGOSEI CO., LTD., Japan). An especially preferred example of a conventional adhesive is Aron Alpha A (which is a medical use adhesive, manufactured and sold by TOAGOSEI CO., LTD., Japan).

Anchors 6,6 may be produced by cutting a commercially available double-sided adhesive tape into an appropriate size. In this case, a double-sided adhesive tape may be used as such or may be used in a form adhered to a resin shaped article or a metallic plate, such as an aluminum plate. An example of a commercially available double-sided adhesive tape is a "Strong Double-Sided Adhesive Tape for interior surfaces (Kyoryoku Ryomen Tape, Hekimen-yo Okunai)" (width: 15 mm; thickness: 2 mm), manufactured and sold by NITOMS, Inc., Japan.

Each of anchors 6,6 may have a structure in which a securing means for securing anchor 6 to a forward free end portion (not in contact with the nail bed) of a nail is present at the forward end of anchor 6, which corresponds to the forward end of a nail. Examples of such securing means include a clip-like securing means which serves to hold, by pinching, a forward free end portion of a nail, and a pin-like securing means which serves to hold a forward free end portion of a nail by inserting a pin into a through-hole formed in the forward free end portion of a nail.

With respect to the method for securing lifting members 5,5 to anchors 6,6, there is no particular limitation as long as anchors 6,6 are not accidentally detached from lifting members 5,5 during the ingrown nail correction using the apparatus of the present invention. For example, lifting members 5,5 may be adhered to anchors 6,6 by an adhesive. When anchor 6 is a resin shaped article, anchor 6 and lifting members 5,5 may be integrally formed by molding. When anchor 6 is made of a double-sided adhesive tape, one end of string-like lifting member 5 may be wound around the double-sided adhesive tape used as anchor 6 for securing the former to the latter. Further, there may be used a securing method in which a string-like lifting member 5 is tied to anchor 6 using through-holes formed in anchor 6. For example, this method can be practiced as follows. A metallic plate having two through-holes is provided, and one end of string-like lifting member 5 is passed through the two through-holes of the metallic plate so as to form a loop and then is knotted to itself above one surface of the metallic plate, whereupon a double-sided adhesive tape is adhered to the other surface of the metallic plate so as to form anchor 6 composed of the metallic plate having adhered thereto the adhesive tape.

In the apparatus shown in FIG. 3, lifting angle maintenance means 4 has, at both end portions thereof, three guiding through-holes 4a, 4a, 4a each for receiving one of lifting members 5,5, and lifting members 5,5 are inserted in guiding through-holes 4a,4a and have the upper ends thereof secured above the upper openings of guiding through-holes 4a,4a. In FIG. 3, lifting members 5,5 are inserted in guiding through-holes 4a,4a which are positioned most remote from upstanding push-down member 3; however, any appropriate guiding through-holes 4a,4a may be used in accordance with the desired value of the inclination angle A.

In the apparatus shown in FIG. 3, lifting members 5,5 have the upper ends thereof secured to lifting member-securing central rod 9 (of the below-described lifting force adjusting means) positioned above the upper openings of guiding through-holes 4a,4a. However, alternatively, the upper ends of lifting members 5,5 may be secured to upstanding push-down member 3 or lifting angle maintenance means 4. For example, the securing of the upper ends of lifting members 5,5 to lifting angle maintenance means 4 may be performed by a method in which lifting members 5,5 are inserted in guiding through-holes 4a,4a of lifting angle maintenance means 4 and are placed under tension, whereupon the upper ends of lifting members 5,5 are secured, e.g. by tying, to lifting angle maintenance means 4.

With respect to the distance between (the nail-contacting surface of) push-down head 3a of upstanding push-down member 3 and lifting angle maintenance means 4, there is no particular limitation. However, the distance is generally 0 to 5.0 cm, preferably 0.5 to 4.0 cm, more preferably 1.0 to 3.0 cm. When this distance is 0 cm, it means that, as in the case of the apparatus shown in FIG. 6 as described below, a part of lifting angle maintenance means 4 is in contact with the middle portion of the outer surface of nail 2 and serves as upstanding push-down member 3.

The strength of the lifting forces exerted by lifting member 5,5 may be adjusted by the lifting force adjusting means as described below. However, the strength of the lifting forces of lifting member 5,5 may also be adjusted simply by, for example, a method in which lifting members 5,5 are placed under appropriate tension, and the upper ends of lifting members 5,5 are secured, e.g. by tying, to lifting angle maintenance means 4.

It is preferred that the apparatus of the present invention further comprises a lifting force adjusting means which is secured to upstanding push-down member 3 and lifting members 5,5, wherein, in use of the apparatus, the lifting force adjusting means is operated to change the vertical positions of lifting members 5,5 relative to push-down head 3a of upstanding push-down member 3, thereby adjusting the lifting forces of lifting members 5,5.

The lifting force adjusting means as shown in FIG. 3 comprises nut means 7, helical compression spring means 8 and lifting member-securing central rod 9 extending horizontally which are disposed on each other in this order, to thereby form a 'nut/spring/rod' vertical stack, lifting member-securing central rod 9 having both ends thereof which are, respectively, secured to the upper ends of lifting members 5,5, lifting member-securing central rod 9 having a thicknesswise extending through-hole at its center portion of the length thereof, wherein upstanding push-down member 3 has vertically extending rod-like shape 3b and has a threaded top portion which is movably screw-wise inserted into and through nut means 7 and movably non-screw-wise inserted into and through helical compression spring means 8 and the through-hole of lifting member-securing central rod 9, thereby proving a structure in which the threaded top portion of upstanding push-down member 3 is vertically inserted into and through the 'nut/spring/rod' vertical stack, wherein, in use of the apparatus, the 'nut/spring/rod' vertical stack is caused to serve as the lifting force adjusting means by screw-wise turning nut means 7 in either direction to move the position of nut means 7 upward or downward, thereby moving the position of lifting member-securing central rod 9 upward or downward through helical compression spring means 8 functioning as a mechanical cushion between nut means 7 and lifting member-securing central rod 9.

With respect to nut means 7 and helical compression spring means 8, there is no particular limitation, and they can be selected from various types of commercially available nuts and compression springs. With respect to lifting member-securing central rod 9, there is no particular limitation as long as it can sustain the stress applied from both lifting members 5,5 and helical compression spring means 8. Lifting member-securing central rod 9 can be selected from metal rods and resin rods of various shapes (i.e., various cross-sectional shapes, such as a circle, an ellipse, a square and a rectangle). With respect to the size of lifting member-securing central rod 9, there is no particular limitation as long as the desired function can be exhibited. However, the length of lifting member-securing central rod 9 is preferably 2.0 to 10.0 cm, more preferably 3.0 to 8.0 cm, still more preferably 4.0 to 7.0 cm. The diameter, major axis or maximum diameter of lifting member-securing central rod 9 is preferably 0.5 to 2.5 cm, more preferably 0.5 to 1.5 cm, still more preferably 0.5 to 1.0 cm.

Figure 4:
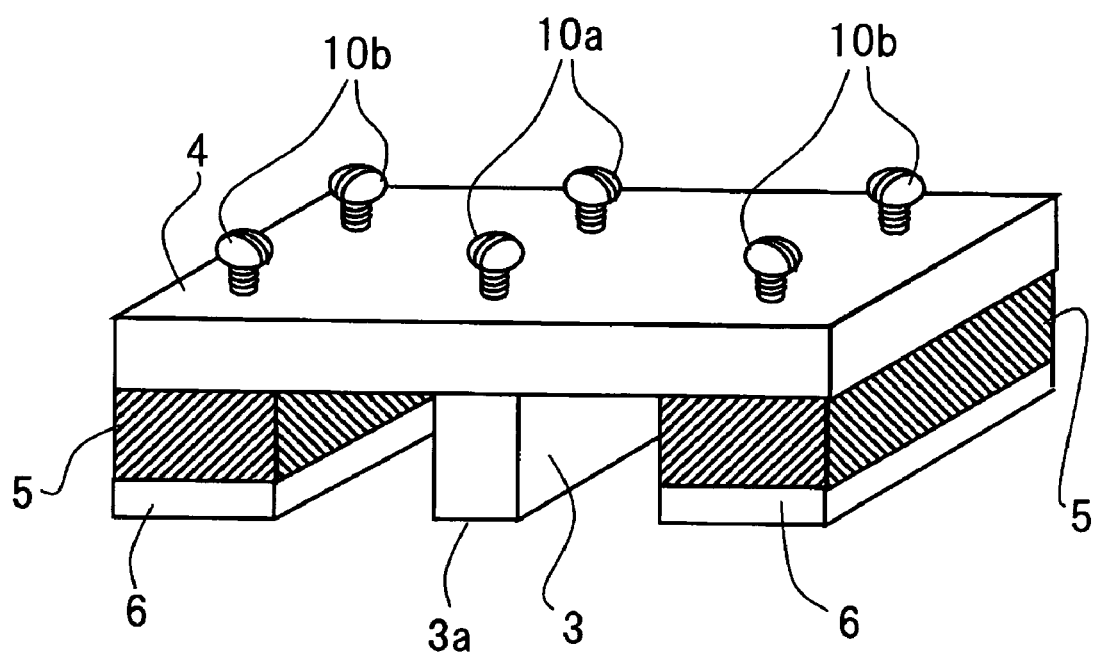
FIG. 4 is a perspective view of another embodiment of the apparatus of the present invention.

FIG. 4 is a perspective view of another embodiment of the apparatus of the present invention. In the apparatus of FIG. 4, each of lifting members 5,5 has a plate-like shape (or block-like shape). The height of upstanding push-down member 3 is adjustable using external screws 10a,10a for securing an upstanding push-down member. The heights of lifting members 5,5 are adjustable using external screws 10b,10b for securing a lifting member. This embodiment may be realized by, for example, a method using lifting angle maintenance means 4 having a plate-like shape which is made of a resin having a relatively high hardness or a metal, wherein the ingrown nail-correcting, lifting force is obtained by causing the lifting members 5,5 to be lifted by external screws 10b, 10b. Alternatively, this embodiment may also be realized by a method using lifting angle maintenance means 4 having a plate-like shape which is made of a resilient body, such as rubber, wherein both ends of plate-like, lifting angle maintenance means 4 (having lifting member 5 at both ends thereof) are resiliently bent down, and then lifting members 5,5 are resiliently attached to the side portions of the outer surface of the nail, thereby exerting an ingrown nail-correcting, lifting force on each of the side portions of the nail. In this case where lifting angle maintenance means 4 is made of a resilient body, lifting angle maintenance means 4 may be formed integrally with lifting members 5,5.

Figure 5:
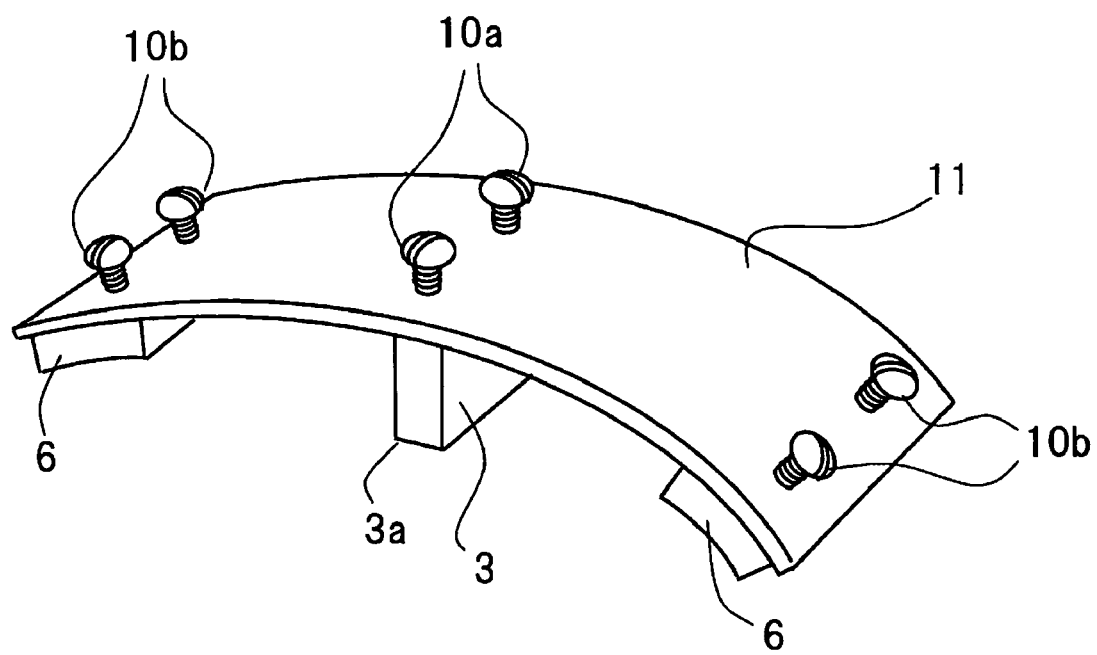
FIG. 5 is a perspective view of still another embodiment of the apparatus of the present invention.

FIG. 5 is a perspective view of still another embodiment of the apparatus of the present invention. In this embodiment, there is employed a means (which is named as a "lifting angle maintenance/tension means") which exhibits the functions of both lifting angle maintenance means 4 and lifting members 5,5. More specifically, in this embodiment of the present invention, there is provided an apparatus for correcting an ingrown nail by lifting a nail edge grown into a nail bed, which comprises:

upstanding push-down member 3 having at a lower end thereof push-down head 3a;

laterally extending, resilient, lifting angle maintenance means 11 which is secured, at a middle portion thereof, to upstanding push-down member 3; and a pair of anchors 6,6 which are respectively secured to the lower surface of lifting angle maintenance means 11 at portions thereof which are opposite relative to the middle portion of lifting angle maintenance means 11 at which upstanding push-down member 3 is secured, wherein, in use of the apparatus:

the apparatus is installed on an outer surface of a nail in a manner such that push-down head 3a of upstanding push-down member 3 contacts a middle portion of the outer surface of the nail, that opposing end portions of resilient, lifting angle maintenance means 11 are bent downward to bring anchors 6,6 into contact with the outer surface of the nail at side portions thereof which are opposite relative to the middle portion at which push-down head 3a of upstanding push-down member 3 contacts the outer surface of the nail, as viewed from the tip of a finger having the nail, and that anchors 6,6 are, respectively, secured to the side portions of the outer surface of the nail, to thereby lift anchors 6,6 under resilient tension caused by the bent lifting angle maintenance means 11 to exert an ingrown nail-correcting, lifting force on each of the side portions of the outer surface of the nail while causing upstanding push-down member 3 to push the middle portion of the outer surface of the nail in the thicknesswise direction of the nail.

As resilient, lifting angle maintenance means 11, the so-called "leaf spring" can be used. With respect to the leaf spring, there is no particular limitation as long as there can be obtained a tension sufficient for correcting an ingrown nail. The material for the leaf spring can be any of a metal and a resilient resin, such as rubber.

A most simple example of the above-mentioned embodiment is as follows. As anchors 6,6, pieces of a double-sided adhesive tape are used. As resilient, lifting angle maintenance means 11 (having upstanding push-down member 3), a leaf spring (having upstanding push-down member 3) is used. The pieces of a double-sided adhesive tape as anchors 6,6 are adhered to appropriate positions of the leaf spring in consideration of the shape and size of the ingrown nail. The length of the leaf spring as resilient, lifting angle maintenance means 11 is preferably 2.5 to 15.0 cm, more preferably 3.0 to 10.0 cm, still more preferably 3.5 to 7.0 cm. The width of the leaf spring as resilient, lifting angle maintenance means 11 is preferably 1.0 to 5.0 cm, more preferably 1.5 to 4.0 cm, still more preferably 2.0 to 3.5 cm.

With respect to the apparatus shown in FIG. 5, the parts and members other than resilient, lifting angle maintenance means 11 may be replaced by the similar pars and members as shown in FIGS. 3 and 4.

Figure 6:
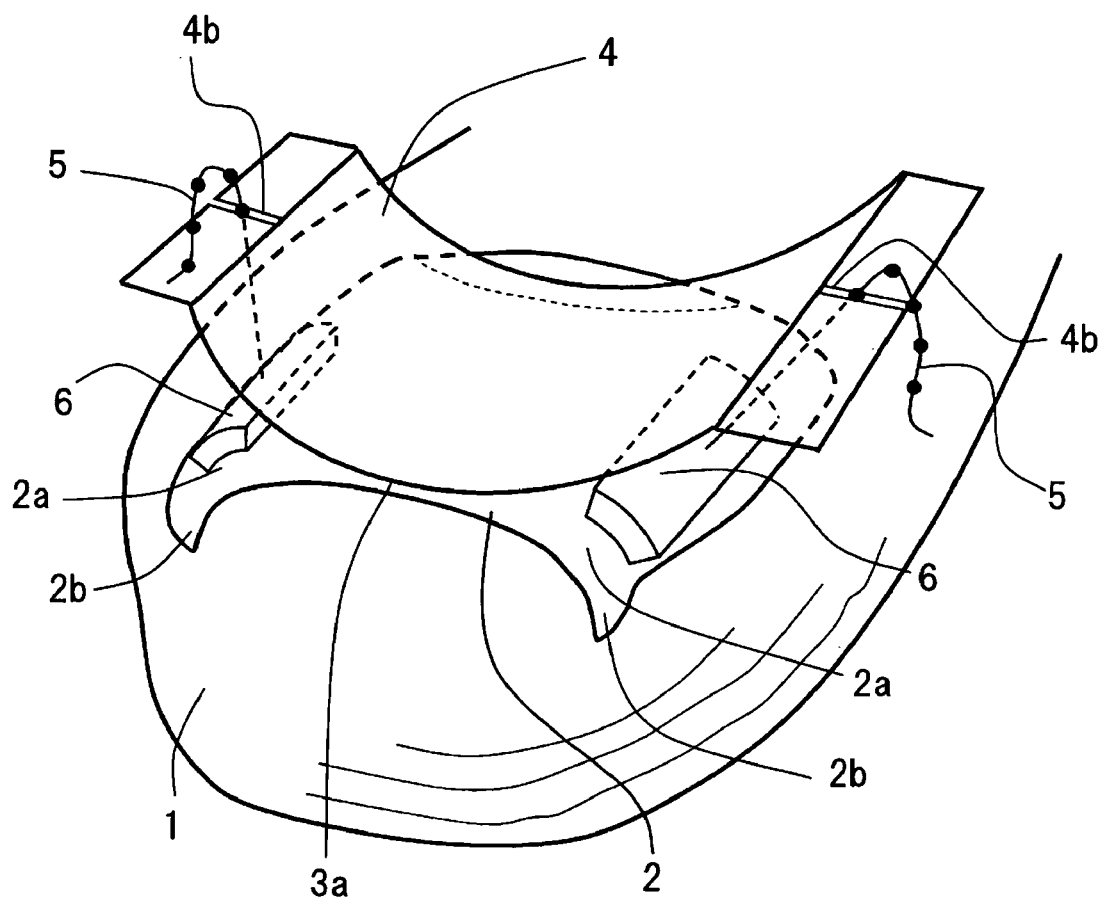
FIG. 6 is a perspective view of a further embodiment of the apparatus of the present invention.

FIG. 6 is a perspective view of a further embodiment of the apparatus of the present invention. In this embodiment, lifting angle maintenance means 4 has a U-like shape, and the bottom of the U-like shape of lifting angle maintenance means 4 is directly contacted with the middle portion of the outer surface of ingrown nail 2, so that lifting angle maintenance means 4 serves also as push-down member 3, and the bottom surface of the U-like shape of lifting angle maintenance means 4 serves as push-down head 3a. U-like shaped lifting angle maintenance means 4 has at ends thereof plate-like portions respectively having slits 4b,4b for holding lifting members 5,5. Each of lifting members 5,5 is independently selected from the group consisting of a flexible linear body and a flexible rod. Each of lifting members 5,5 has a plurality of granular, diameter-increased portions used for engagement with slits 4b,4b. These granular, diameter-increased portions of lifting members 5,5 may be, for example, knots or the like, when lifting members 5,5 are strings or the like. In use of the apparatus shown in FIG. 6, the apparatus is installed on an ingrown nail so that U-like shaped lifting angle maintenance means 4 extends in the widthwise direction of the finger having the nail; the bottom surface (push-down head 3a) of U-like shape of the lifting angle maintenance means 4 is contacted with the middle portion of the outer surface of ingrown nail 2; and anchors 6,6 are, respectively, secured to side portions 2a,2a of the outer surface of ingrown nail 2 (side portions 2a,2a being opposite relative to the longitudinal central axis of the finger). Then, lifting members 5,5 secured to ingrown nail 2 are placed under appropriate tension, and the granular, diameter-increased portions of lifting members 5,5 are caused to be engaged with slits 4b,4b of U-like shaped lifting angle maintenance means 4, so as to secure the upper portions of lifting members 5,5 to U-like shaped lifting angle maintenance means 4, thereby exerting an ingrown nail-correcting, lifting force on each of side portions 2a,2a of the outer surface of ingrown nail 2 through anchors 6,6 while causing push-down head 3a to push the middle portion of the outer surface of ingrown nail 2 in the thicknesswise direction of ingrown nail 2.

FIG. 7 is a perspective view of still a further embodiment of the apparatus of the present invention. The apparatus of the present invention shown in FIG. 7 has a pair of belt-like lifting members 5,5 having a securing function as in the case of tying bands (the so-called "cable ties") or the like. The apparatus shown in FIG. 7 has also a pair of supplemental lifting members 5a,5a. In this apparatus, lifting angle maintenance means 4 has an inverted U-like shape which corresponds to the curvature of a nail. Lifting angle maintenance means 4 has three guiding through-holes 4a, 4a, 4a at both ends thereof, the guiding through-holes being used for inserting therein lifting members 5,5 and supplemental lifting members 5a,5a. Lifting members 5,5 and supplemental lifting members 5a,5a are, respectively, inserted in guiding through-holes 4a, 4a, 4a, 4a. Lifting members 5,5 are also inserted in and through helical compression spring means 8,8 disposed on and above lifting angle maintenance means 4. Each helical compression spring means 8 is secured, at its lower end, to the upper opening of guiding through-hole 4a. Each of lifting members 5,5 and supplemental lifting members 5a,5a has nut 8a for securing a helical compression spring means, nut 8a being positioned above helical compression spring means 8.

In the apparatus shown in FIG. 7, main body 3c of upstanding push-down member 3 is threaded and screw-wise inserted into and through lifting angle maintenance means 4. Cross handle 3d is secured to the top portion of threaded main body 3c of upstanding push-down member 3. By turning cross handle 3d, the vertical position of push-down head 3a can be changed relative to lifting angle maintenance means 4.

The apparatus shown in FIG. 7 having the above-described construction is used as follows. The apparatus shown in FIG. 7 is installed on a nail, and cross handle 3d is turned to lower the relative vertical position of push-down head 3a of upstanding push-down member 3 (so as to press on the outer surface of the nail) and simultaneously to raise the relative vertical position of lifting angle maintenance means 4 and lifting members 5,5, thereby lifting side portions 2a,2a of the outer surface of the nail. It is possible to modify this embodiment so that that helical compression spring means 8 is omitted and lifting members 5,5 are directly secured to lifting angle maintenance means 4. However, it preferred to use helical compression spring means 8, since helical compression spring means 8 serves as a cushion which prevents side portions 2a,2a of the outer surface of ingrown nail from sustaining a steep great burden or an unnecessarily long duration of a great burden. More specifically, the use of helical compression spring means 8 is advantageous in that (1), at the time when push-down head 3a of upstanding push-down member 3 is pressed on a middle portion of the outer surface of the ingrown nail, side portions 2a,2a can be prevented from sustaining a steep great burden, and that (2) during the course of the ingrown nail correction, the lifting force exerted on side portions 2a,2a of the outer surface of the ingrown nail is gradually decreased in accordance with the corrective lifting of side portions 2a,2a, so that side portions 2a,2a can be prevented from sustaining an unnecessarily long duration of a great burden. The material for and the dimensions of helical compression spring means 8 (spring height, pitch, wire diameter and coil diameter, and pitch angle) can be appropriately chosen in accordance with the desired level of the lifting force.

Further, as shown in FIG. 7, in a preferred embodiment of the apparatus of the present invention, the apparatus further comprises a pair of supplemental lifting members 5a,5a extending downwardly from respective portions of lifting angle maintenance means 4, which portions are closer to upstanding push-down member 3 than lifting members 5,5, each supplemental lifting member having supplemental anchor 6a at a lower end thereof. Depending on the condition of the ingrown nail (for example, when the nail curvature is relatively large), it is possible that, when only side portions 2a,2a are lifted using lifting members 5,5, the nail is bent like a hinge where the longitudinal central axis of the nail serves as a fulcrum, thus flattening only the curvature of the middle portion of the nail while leaving the curvature of the ingrown side portions of the nail uncorrected or insufficiently corrected. This problem can be solved by employing the above-mentioned supplemental lifting members 5a,5a, thereby surely correcting an ingrown nail. If desired, more than a pair of supplemental lifting members 5a,5a may be used. However, generally, use of only a pair of supplemental lifting members 5a,5a is sufficient for achieving the desired effect.

As in the case of the inclination angle A described above in connection with lifting members 5,5, it is preferred that, when the apparatus is installed on the outer surface of nail 2, each of supplemental lifting members 5a,5a extends downwardly from supplemental lifting angle maintenance means 4 in a vertical direction or a direction inclined toward the longitudinal central axis of nail 2. The vertical direction is defined as the thicknesswise direction of the finger having the nail. Further, when each of supplemental lifting members 5a,5a extends downwardly from lifting angle maintenance means 4 in a direction inclined toward the longitudinal axis of nail 2, an appropriate inclination angle A' relative to the vertical direction, as measured at the connection point between supplemental lifting member 5a and supplemental anchor 6a, varies depending on, e.g., the degree of curvature of and the hardness of the ingrown nail. However, it is preferred that the inclination angle A' is at least 10°, more advantageously at least 20° relative to the vertical direction, as measured at the connection point between supplemental lifting member 5a and supplemental anchor 6a. However, from the viewpoint of achieving effective correction of an ingrown nail, it is preferred that the inclination angle A' of supplemental lifting members 5a,5a is smaller than the inclination angle A of lifting members 5,5. The difference between the inclination angle A' and the inclination angle A may be appropriately selected within a range which is suitable for achieving effective correction of an ingrown nail. However, the difference between the inclination angle A' and the inclination angle A is preferably 1 to 20°, more preferably 2 to 15°, still more preferably 5 to 12°. The inclination angle A' is as measured after the installation of the apparatus of the present invention on ingrown nail 2 and before the commencement of the nail correcting operation by placing the lifting members 5,5 and supplemental lifting members 5a,5a under tension.

The distance between supplemental lifting members 5a,5a may vary depending on the size of the entire apparatus and the size of a nail to be corrected. However, the distance between supplemental lifting members 5a,5a is preferably 50 to 90%, more preferably 60 to 85%, still more preferably 60 to 80%, in terms of the percentage relative to the distance between lifting members 5,5.

With respect to the material, shape and dimensions of supplemental lifting members 5a,5a, they may be the same as those of lifting members 5,5. Also, with respect to the material, shape and dimensions of supplemental anchors 6a,6a, they may be the same as those of anchors 6,6. However, in general, the lifting efficiency of supplemental lifting members 5a,5a may be smaller than that of lifting members 5,5; therefore, supplemental anchors 6a,6a may be smaller in dimensions than anchors 6,6.

FIG. 8 is a perspective view of still another further embodiment of the apparatus of the present invention. The apparatus shown in FIG. 8 has lifting angle maintenance means 4 having movable wings. This lifting angle maintenance means 4 comprises main body 4c, a pair of movable wings 4d,4d extending from the main body, lifting member-securing plates 4e,4e respectively secured to movable wings 4d,4d.

Movable wings 4d,4d are connected to main body 4c so that movable wings 4d,4d are pivotally, vertically movable (as indicated by the arrows shown in FIG. 8). This arrangement enables the adjustment of the inclination angle A. Main body 4c has, attached thereto, external screws (not shown) for securing movable wings, and these external screws can secure movable wings 4d,4d at a desired angle.

Lifting member-securing plates 4e,4e are laterally slidable, so that the lifting interval can be adjusted. Lifting member-securing plates 4e,4e have, attached thereto, external screws (not shown) for securing themselves, and these external screws can secure lifting member-securing plates 4e,4e at a desired position.

With respect to the specific shapes of the components of lifting angle maintenance means 4 shown in FIG. 8, there is no particular limitation as long as lifting angle maintenance means 4 exhibits the desired functions. Further, with respect to lifting members 5,5 and anchors 6,6, there is no particular limitation. The shapes and dimensions of lifting members 5,5 and anchors 6,6 can be appropriately selected from those as described above.

There can be provided a system for correcting an ingrown nail, which is able to decrease the limitations on the activity of an ingrown nail patient undergoing the ingrown nail correction using the apparatus of the present invention. The system for correcting an ingrown nail comprises:
the apparatus of the present invention,
a heat insulation chamber which is positioned on and integrally formed with the lifting angle maintenance means,
a heater accommodated in the heat insulation chamber, and
a small size thermostat,
wherein:
a sensor of the small size thermostat is disposed in the heat insulation chamber, and
the upstanding push-down member has a high heat conductivity and is in contact with the heater.

In the use of the above-mentioned system for correcting an ingrown nail, the small size thermostat is secured to, for example, the ankle of the patient by a fastening device, such as a belt, thereby enabling the nail correction without limiting the activity of the patient. As mentioned above, by the use of the apparatus of the present invention, an ingrown nail can be surely corrected within a very short time, thereby greatly reducing a burden on the patient. Further, by using the system mentioned above, a burden on the patient can be further reduced.

With respect to the shape, material and dimensions of the heat insulation chamber of the system, there is no particular limitation. However, it is preferred that the shape, material and dimensions of the heat insulation chamber are selected from those which ensure that a burden on a patient is as low as possible. For example, as a small size thermostat, there may be used METIII or METII, manufactured and sold by Matsuo Electric Co., Ltd. Japan.

Next, a method for correcting an ingrown nail by using the apparatus of the present invention is explained.

The correction of an ingrown nail by using the apparatus of the present invention is especially effective when the nail correction is performed with respect to the nail which has been softened by using a nail softening agent comprising a protein degrading substance. For example, as a nail softening agent, there can be used a correction reagent described in Patent Document 4. In Patent Document 4, the correction reagent is limited to at least one reducing agent selected from the group consisting of cysteine, thioglycolic acid and thioglycolate. However, in the present invention, the nail softening agent is not particularly limited as long as the nail softening agent functions as a reducing anent for the disulfide bonds of the keratin protein of a nail and the reducing power thereof is suitable for the purpose of nail softening. The correction of a nail which has been softened by such a nail softening agent by using the apparatus of the present invention can, for example, be performed by the following method.
(1) Anchors 6,6 are, respectively, adhered to the outer surface of nail 2 at side portions 2a,2a thereof which are opposite relative to the middle portion of nail 2. (If desired, supplemental anchors 6a,6a are, respectively, adhered to the outer surface of nail 2 at portions thereof which are closer to the middle portion of nail 2 than side portions 2a,2a.)

(2) Lifting members 5,5 (or lifting angle maintenance means 11) (and optionally supplemental lifting members 5a,5a) are placed under tension, thereby exerting and maintaining a lifting force on anchors 6,6 (and optionally supplemental anchors 6,6) adhered to side portions 2a,2a.

(3) The nail softening agent is applied to the outer surface of nail 2.

(4) The foot having finger 1 is entirely covered with a vinyl bag or the like, and the resultant is immersed in a footbath having a temperate of 40 to 50° C., thereby causing ingrown nail 2 to be softened while lifting side portions 2a,2a of the outer surface of ingrown nail 2 to pull out ingrown portions 2b,2b from the nail grooves.

(5) After a period of about 30 minutes, the foot is taken out from the footbath, the vinyl bag is removed, and the apparatus of the present invention is removed from nail 2.

(6) The foot is washed with water and then dried. An oxidizing agent is applied to nail 2, thereby causing nail 2 to be hardened in a state in which ingrown portions 2b,2b have been pulled out from the nail grooves.

Steps (2) and (3) may be performed in the reverse order.

With respect to the above-mentioned nail-softening agent (reducing agent for disulfide-linkages) and oxidizing agent, commercially available agents for permanent wave (the so-called permanent wave solutions) can be used. More specifically, the 1st agent of such permanent wave solutions can be used as the nail-softening agent, and the 2nd agent of such permanent wave solutions can be used as the oxidizing agent. As a specific example of the permanent wave solutions, there can be mentioned 1st agent (white cream-like liquid composed mainly of a thioglycolate) and 2nd agent (white cream-like liquid composed mainly of hydrogen peroxide) of "Venezel Men's Straight Perm" manufactured and sold by Dariya Corporation, Japan.

The above-mentioned nail-softening agent and the oxidizing agent may be used in respective amounts such that the exposed portions of a nail which are not covered with anchors 6,6 (and supplemental anchors 6a,6a) can be thoroughly coated with the nail-softening agent and the oxidizing agent. Appropriate amounts of the nail-softening agent and the oxidizing agent vary depending on the types of these agents, size of the nail, etc.; however, each of these agents is generally used in an amount of 1 to 5 g per nail. Further, with respect to the application of the nail-softening agent and the oxidizing agent to a nail, there is no particular limitation with respect to the method therefor, and the application may be effected by any appropriate method, such as application by a brush.

Further, with respect to the pulling force applied to anchors 6,6, appropriate pulling force may vary depending on the severeness of the ingrown nail, the above-mentioned angle A, the shape and hardness of the nail, etc., but is generally in the range of from 200 to 1,000 gf, preferably from 250 to 800 gf, more preferably from 300 to 600 gf.

The apparatus of the present invention may also be used in a case where only one side of a nail has been ingrown into a nail bed. In such a case, for example, by installing the apparatus on an ingrown nail in a manner such that the push-down member contacts the nail at a position which is biased from the longitudinal axis of the nail toward the ingrown side of the nail, the ingrown nail may be corrected more effectively. When the apparatus is installed at such a biased position of the nail, there is no particular limitation with respect to the position, size and shape of the other anchor which is attached to the side of the nail which is not ingrown, as long as the balance of the apparatus can be maintained during the ingrown nail correction treatment using the apparatus. For example, the other anchor may be smaller in size than the anchor attached to the ingrown side of the nail, and may be attached around the center of the nail.

Further, the ingrown nail correction using the above-mentioned system can be performed by the same method as mentioned above except that the footbath and the plastic bag (for covering the foot) are not needed.

EXAMPLES

Hereinbelow, the present invention will be explained in more detail with reference to the following Examples, which should not be construed as limiting the scope of the present invention.

Example 1

Using an ingrown nail correcting apparatus of the present invention as shown in FIG. 3, two patients (a 39 year old female and a 32 year old male) having mild or moderate ingrown first toenails were treated as explained below. In the case of the 39 year old female patient, both side portions of each of the first toenails had been bent downwardly and grown into the nail bed to a depth of about 1 mm. In the case of the 32 year old male patient, both side portions of each of the first toenail had been bent downwardly and grown into the nail bed to a depth of about 2 mm.

(Reducing Agent and Oxidizing Agent)

The reducing agent and oxidizing agent used in the Examples were as follows.

Reducing agent: 1st agent (white cream-like liquid composed mainly of a thioglycolate) of "Venezel Men's Straight Perm" manufactured and sold by Dariya Corporation, Japan Oxidizing agent: 2nd agent (white cream-like liquid composed mainly of hydrogen peroxide) of "Venezel Men's Straight Perm" manufactured and sold by Dariya Corporation, Japan (Construction of the Ingrown Nail Correcting Apparatus)

As lifting members 5,5, two nylon strings (diameter: 1.0 mm) were used. As anchors 6,6, two rectangular resin shaped articles (length: 10 mm, width: 7 mm, and height: 3 mm), each having adhered to the bottom thereof a double-sided adhesive tape having a thickness of 2 mm (strong double-sided adhesive tape for interior surfaces, manufactured and sold by Nitoms Inc., Japan) (cut into a rectangular shape having a length of 10 mm and a width of 7 mm), were used. With respect to each of lifting members 5,5 (nylon strings), one end thereof was attached to an upper portion of anchor 6. The interval between lifting members 5,5 as measured at positions of contacts between lifting members 5,5 and the bottom surface of lifting angle maintenance means 4 was 5 cm.

(Operation)

The ingrown nail correcting apparatus was installed on the ingrown nail of the patient as follows. Anchors 6,6 of the ingrown nail correcting apparatus were attached to both side portions 2a,2a of ingrown nail 2 of the patient. Then, the free ends of lifting members 5,5 (nylon strings) attached to anchors 6,6 were inserted into and penetrated through through-holes 4a,4a formed at end portions of lifting angle maintenance means 4. To the end portions of lifting member-securing central rod 9 were, respectively, attached the above-mentioned free ends of lifting members 5,5 so as to prevent the loosening of lifting members 5,5. Then, screw 7 was turned anticlockwise as viewed from above screw 7 to thereby elevate lifting member-securing central rod 9 gradually through helical compression spring means 8 so that anchors 6,6 which were respectively attached to side portions 2a,2a of ingrown nail 2 were pulled at a nail-correcting force of 250 to 300 gf. The inclination angle A of each of lifting members 5,5 was 45°, and the lifting interval was 2.5 in terms of a ratio of the distance between lifting members 5,5 as measured at positions of contacts between lifting members 5,5 and lifting angle maintenance means 4, relative to the width of the nail on which the apparatus was installed.

Using the thus installed apparatus, a treatment for correcting the ingrown nail was performed as follows. About 5 g of the reducing agent was applied to the surface of the nail at portions thereof which were not covered by anchors 6,6 and push-down head 3a, and the foot having the ingrown nail was inserted into a transparent plastic bag and the opening of the bag was closed around the ankle of the foot by tightening with a string in a manner such that water would not intrude into the bag. The foot in the bag was put into a footbath having a temperature of about 40° C., and allowed to stand for 30 minutes. Then, the foot was taken out of the footbath and the plastic bag, followed by washing with water to remove the reducing agent. To the nail of the foot was applied about 5 g of the oxidizing agent, and the nail was allowed to stand for 15 minutes. Then, the ingrown nail-correcting apparatus was detached from the nail, followed by washing the foot with water to remove the oxidizing agent. Each first toenail of each of the two patients was treated by the same operation as mentioned above. With respect to both of the two patients, 7 days and 30 day after the ingrown nail-correction treatment, the treated nails were observed. As a result, it was confirmed that side portions 2a,2a of each nail 2 of the patients had been pulled out from the respective nail grooves, and each nail 2 had a normal shape, so that the ingrown nails of both of the patients were corrected.

Example 2

Using the ingrown nail-correcting apparatus as shown in FIG. 7, a patient (a 72 year old female) having severe ingrown first toenails was treated as explained below. Specifically, both side portion of each of the first toenails had been bent downwardly and grown into the nail bed to a depth of about 3 mm.

The treatment for correcting the ingrown nails was performed in the same manner as in Example 1 except that the apparatus as shown in FIG. 7 was used. In the apparatus of FIG. 7, commercially available resin cable ties (each having a width of 2 mm) are used as lifting members 5,5 and supplemental lifting members 5a,5a. To one end of each of lifting members 5,5 was attached, as anchor 6, a rectangular resin shaped article having a length of 8 mm, a width of 3 mm and a height of 2 mm, which had adhered at the bottom thereof a double-sided adhesive tape having a thickness of 2 mm (strong double-sided adhesive tape for interior surfaces, manufactured and sold by Nitoms Inc., Japan) (cut into a rectangular shape having a length of 8 mm and a width of 3 mm). Each of lifting members 5,5 and supplemental lifting members 5a,5a was inserted into and penetrated through helical compression spring means 8. To upper portions of helical compression spring means 8, 8, 8, 8 were attached lifting members 5,5 and supplemental lifting members 5a,5a by nuts 8a, 8a, 8a, 8a, respectively. Further, each helical compression spring means 8 was, at a lower portion thereof, attached to lifting angle maintenance means 4 around through-hole 4a so that lifting member 5 or supplemental lifting member 5a (passing through the above-mentioned through-hole 4a) was supported above lifting angle maintenance means 4 by helical compression spring means 8 in a manner such that lifting member 5 or supplemental lifting member 5a was movable downward and upward through helical compression spring means 8. The interval between lifting members 5,5 as measured at positions of contacts between lifting members 5,5 and the bottom surface of lifting angle maintenance means 4 was 3.7 cm, and the interval between supplemental lifting members 5,5 as measured at positions of contacts between lifting members 5,5 and the bottom surface of lifting angle maintenance means 4 was 1.6 cm.

(Operation)

The first toenail of the right foot of the patient was treated in the same manner as in Example 1 without using supplemental lifting members 5a,5a. As a result, it was found that the side portions of the nail were lifted upward by bending where the longitudinal central axis of the nail served as a fulcrum, but only the center portion of the nail was flattened and the anomalous curvature at each of the side portions of the nail was not satisfactorily corrected. Therefore, the same operation as mentioned above was performed using supplemental lifting members 5a,5a as well as lifting members 5,5. As a result, it was found that ingrown side portions 2a,2a were completely corrected, and the nail had a normal shape.

Further, the first toenail of the left foot of the patient was treated in the same manner as in Example 1 using not only lifting members 5,5 but also supplemental lifting members 5a,5a. As a result, it was found that ingrown side portions 2a,2a were completely corrected, and the nail had a normal shape.

The inclination angle A of each of lifting members 5,5 was 85°, and the lifting interval was 2.47 in terms of a ratio of the distance between lifting members 5,5 as measured at positions of contacts between lifting members 5,5 and lifting angle maintenance means 4, relative to the width of the nail on which the apparatus was installed. Further, the inclination angle A of each of supplemental lifting members 5a,5a was 27.5°, and the lifting interval was 1.07 in terms of a ratio of the distance between supplemental lifting members 5a,5a as measured at positions of contacts between supplemental lifting members 5a,5a and lifting angle maintenance means 4, relative to the width of the nail on which the apparatus was installed.

INDUSTRIAL APPLICABILITY

By the use of the apparatus of the present invention, an ingrown nail can be surely corrected within a very short time, e.g., within about 30 minutes to about 1 hour, with a very simple operation and without causing pain to a patient. Therefore, the apparatus of the present invention is very effective and, hence, has a very high practicality.

The invention claimed is:

1. An apparatus for correcting an ingrown nail by lifting a nail edge grown into a nail bed, which comprises:
   an upstanding push-down member having at a lower end thereof a push-down head;
   a laterally extending, lifting angle maintenance means which is secured, at a middle portion thereof, to said upstanding push-down member; and
   a pair of lifting members extending downwardly from respective portions of said lifting angle maintenance means, which portions are opposite relative to said middle portion of the lifting angle maintenance means at which said upstanding push-down member is secured, each lifting member having an anchor at a lower end thereof, wherein said anchor has an adhesive lower surface to be directly contacted with a top surface of a nail, wherein, when said apparatus is installed on the top surface of a nail, each of said lifting members extends downwardly from said lifting angle maintenance means in a direction inclined toward the longitudinal axis of the nail at an inclination angle of at least 10° relative to the vertical direction, as measured at the connection point between said lifting member and said anchor, wherein said vertical direction is defined as the thicknesswise direction of the finger having the nail, and wherein, in use of said apparatus:

said apparatus is installed on the top surface of a nail in a manner such that the push-down head of said upstanding push-down member contacts a middle portion of the top surface of the nail, and that the adhesive lower surfaces of the anchors of the lifting members are, respectively, adhered to the top surface of the nail at side portions thereof which are opposite relative to said middle portion at which said push-down head of the upstanding push-down member contacts the top surface of the nail, as viewed from the tip of a finger having the nail, and when said lifting members are placed under tension, said anchors are lifted to thereby exert an ingrown nail-correcting, lifting force on each of said side portions of the top surface of the nail, while causing the upstanding push-down member to push said middle portion of the top surface of the nail in the thicknesswise direction of the nail; the apparatus having a lifting interval, wherein the lifting interval is 1 or more in terms of a ratio of the distance between said lifting members as measured at positions of contacts between the lifting members and said lifting angle maintenance means, relative to the width of the nail on which said apparatus is installed.

2. The apparatus according to claim 1, wherein said lifting angle maintenance means has guiding through-holes for respectively receiving therethrough said lifting members.

3. The apparatus according to claim 2, wherein said lifting members are, respectively, inserted in said guiding through-holes of said lifting angle maintenance means and engaged with the peripheries of said guiding through-holes, thereby securing said lifting members to said lifting angle maintenance means.

4. The apparatus according to claim 1, wherein said inclination angle is at least 20° relative to the vertical direction.

5. The apparatus according to claim 1, wherein said lifting interval is 1.2 or more.

6. The apparatus according to claim 1, wherein each of said lifting members is independently selected from the group consisting of a flexible linear body and a flexible rod.

7. The apparatus according to claim 1, wherein said lifting members are secured to said upstanding push-down member or said lifting angle maintenance means.

8. The apparatus according to claim 1, wherein:

said upstanding push-down member has a shape selected from the group consisting of a vertically extending rod shape and a plate shape which has both surfaces thereof extending vertically and along the longitudinal direction of the finger having the nail on which said apparatus is installed, and said lifting angle maintenance means has a shape selected from the group consisting of a horizontally extending rod shape, an inverted U or V shape, a U or V shape, and a plate-like shape which has both surfaces thereof extending horizontally.

9. The apparatus according to claim 1, which further comprises a lifting force adjusting means which is secured to said upstanding push-down member and said lifting members, wherein, in use of said apparatus, said lifting force adjusting means is operated to change the lifting member-secured positions thereof upwardly or downwardly relative to the push-down head of said upstanding push-down member, thereby adjusting the lifting forces of said lifting members.

10. The apparatus according to claim 1, which further comprises a pair of supplemental lifting members extending downwardly from respective portions of said lifting angle maintenance means, which portions are closer to said upstanding push-down member than said lifting members, each supplemental lifting member having a supplemental anchor at a lower end thereof, wherein said supplemental anchor has an adhesive lower surface to be directly contacted with a top surface of a nail.

11. An apparatus for correcting an ingrown nail by lifting a nail edge grown into a nail bed, which comprises:

an upstanding push-down member having at a lower end thereof a push-down head;

a laterally extending, lifting angle maintenance means which is secured, at a middle portion thereof, to said upstanding push-down member; and a pair of lifting members extending downwardly from respective portions of said lifting angle maintenance means, which portions are opposite relative to said middle portion of the lifting angle maintenance means at which said upstanding push-down member is secured, each lifting member having an anchor at a lower end thereof, wherein said anchor has an adhesive lower surface to be contacted with an outer surface of a nail, wherein, when said apparatus is installed on the outer surface of a nail, each of said lifting members extends downwardly from said lifting angle maintenance means in a direction inclined toward the longitudinal axis of the nail at an inclination angle of at least 10° relative to the vertical direction, as measured at the connection point between said lifting member and said anchor, wherein said vertical direction is defined as the thicknesswise direction of the finger having the nail, and wherein, in use of said apparatus:

said apparatus is installed on the outer surface of a nail in a manner such that the push-down head of said upstanding push-down member contacts a middle portion of the outer surface of the nail, and that the adhesive lower surfaces of the anchors of the lifting members are, respectively, adhered to the outer surface of the nail at side portions thereof which are opposite relative to said middle portion at which said push-down head of the upstanding push-down member contacts the outer surface of the nail, as viewed from the tip of a finger having the nail, and when said lifting members are placed under tension, said anchors are lifted to thereby exert an ingrown nail-correcting, lifting force on each of said side portions of the outer surface of the nail, while causing the upstanding push-down member to push said middle portion of the outer surface of the nail in the thicknesswise direction of the nail, the apparatus further comprising a lifting force adjusting means which is secured to said upstanding push-down member and said lifting members, wherein, in use of said apparatus, said lifting force adjusting means is operated to change the lifting member-secured positions thereof upwardly or downwardly relative to the push-down head of said upstanding push-down member, thereby adjusting the lifting forces of said lifting members, wherein said lifting force adjusting means comprises a nut means, a helical compression spring means and a lifting member securing central rod extending horizontally which are disposed on each other in this order, to thereby form a 'nut/spring/rod' vertical stack, said lifting member securing central rod having both ends thereof which are, respectively, secured to the upper ends of said lifting members, said lifting member securing central rod having a thicknesswise extending through-hole at its center portion of the length thereof, wherein said upstanding push-down member has a vertically extending rod shape and has a threaded top portion which is movably screw-wise inserted into and through said nut means and movably non-screw-wise inserted into and through said helical compression spring means and said through-hole of said lifting member securing central rod, thereby providing a structure in which the threaded top portion of said upstanding push-down member is vertically inserted into and through said 'nut/spring/rod' vertical stack, wherein, in use of said apparatus, said 'nut/spring/rod' vertical stack is caused to serve as said lifting force adjusting means by screw-wise turning said nut means in either direction to move the position of said nut means upward or downward, thereby moving the position of said lifting member securing central rod upward or downward through said helical compression spring means functioning as a mechanical cushion between said nut means and said lifting member securing central rod.

* * * * *